US012605560B2

(12) United States Patent
     Wong

(10) Patent No.: US 12,605,560 B2
(45) Date of Patent: Apr. 21, 2026

(54) COMPACT PORTABLE ELECTROMAGNETIC FIELD AND ION EMITTER APPARATUS

(71) Applicant: Quantum Biotechnology Corp., Vancouver (CA)

(72) Inventor: Yat Fai Wong, Vancouver (CN)

(73) Assignee: Quantum Biotechnology Corp., Vancouver (CA)

( * ) Notice: Subject to any disclaimer, the term of this patent is extended or adjusted under 35 U.S.C. 154(b) by 1045 days.

(21) Appl. No.: 17/658,851

(22) Filed: Apr. 12, 2022

(65) Prior Publication Data

US 2022/0233876 A1     Jul. 28, 2022

Related U.S. Application Data

(63) Continuation-in-part of application No. 17/033,852, filed on Sep. 27, 2020, now abandoned.

(51) Int. Cl.
     *A61N 2/02*      (2006.01)
     *A61N 2/00*      (2006.01)
     *A61N 5/10*      (2006.01)

(52) U.S. Cl.
     CPC .............. *A61N 2/02* (2013.01); *A61N 2/002* (2013.01); *A61N 5/10* (2013.01); *A61N 2005/1087* (2013.01)

(58) Field of Classification Search
     CPC .......... A61M 2021/0055; A61M 21/00; A61M 21/02; A61M 2/002; A61M 2/02
     See application file for complete search history.

(56) References Cited

U.S. PATENT DOCUMENTS

| | | | |
|---|---|---|---|
| 4,020,590 A | 5/1977 | Davis | |
| 4,535,775 A | 8/1985 | Brighton et al. | |
| 5,402,782 A | 4/1995 | Lodder | |
| 5,553,610 A | 9/1996 | Lodder | |
| 6,099,459 A | 8/2000 | Jacobson | |
| 6,210,317 B1 | 4/2001 | Bonlie | |
| 6,280,376 B1 | 8/2001 | Holcomb | |
| 9,812,246 B1 | 11/2017 | Nunez et al. | |
| 2002/0103411 A1 | 8/2002 | Bailey et al. | |
| 2013/0211181 A1* | 8/2013 | Schmidt ................ A61N 2/002 600/13 |

(Continued)

OTHER PUBLICATIONS

Qi Coil | PEMF Therapy; retrieved Jun. 25, 2021; https://info.qicoil.com/limited-time-special/; 10 pages.

(Continued)

*Primary Examiner* — Christine H Matthews
(74) *Attorney, Agent, or Firm* — Perkins Coie LLP

(57) ABSTRACT

An apparatus includes a torus-shaped mount and a coil including a conducting wire wound around the mount such that the coil has an inductance. The coil is configured to generate electromagnetic fields based on the inductance when electrical signals pass through the coil. The electromagnetic fields have frequencies in an Extremely Low Frequency (ELF) range and a Very Low Frequency (VLF) range. The electromagnetic fields provide therapy to a user. A clip is affixed to the mount and encases terminal ends of the wire. The clip is configured to receive the electrical signals from a user device and pass the electrical signals to the coil via the terminal ends.

17 Claims, 23 Drawing Sheets

(56) References Cited

U.S. PATENT DOCUMENTS

| 2014/0161294 | A1 | 6/2014 | Haymond |
| 2019/0269877 | A1 | 9/2019 | Wong |
| 2021/0008381 | A1 | 1/2021 | Wong |

OTHER PUBLICATIONS

Qi Coil Matrix; https://www.qicoilmatrix.com/; retrieved from the Internet on Apr. 26, 2022; 9 pages.

\* cited by examiner

110

100

106

104

108

102

602

1100

1104

1108

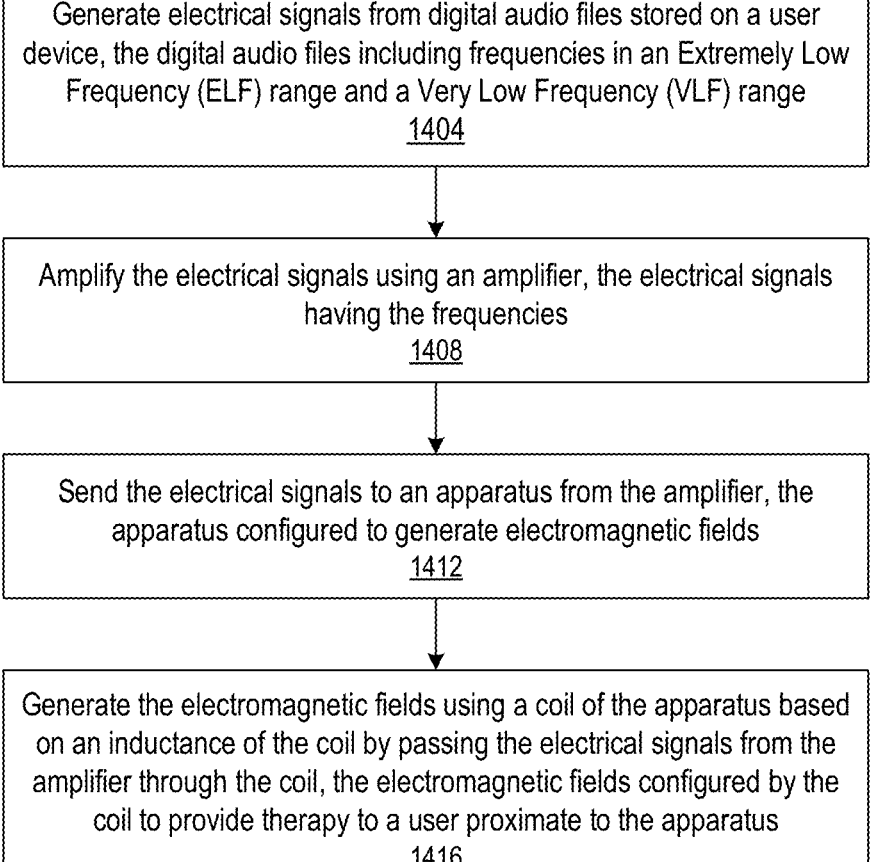

Generate electrical signals from digital audio files stored on a user device, the digital audio files including frequencies in an Extremely Low Frequency (ELF) range and a Very Low Frequency (VLF) range
1404

Amplify the electrical signals using an amplifier, the electrical signals having the frequencies
1408

Send the electrical signals to an apparatus from the amplifier, the apparatus configured to generate electromagnetic fields
1412

Generate the electromagnetic fields using a coil of the apparatus based on an inductance of the coil by passing the electrical signals from the amplifier through the coil, the electromagnetic fields configured by the coil to provide therapy to a user proximate to the apparatus
1416

COMPACT PORTABLE ELECTROMAGNETIC FIELD AND ION EMITTER APPARATUS

CROSS-REFERENCE TO RELATED APPLICATIONS

This application is a continuation-in-part application of U.S. patent application Ser. No. 17/033,852, filed Sep. 27, 2020, which claims the benefit of U.S. Provisional Patent Application No. 62/861,964, filed Jun. 14, 2019, both of which are incorporated by reference herein in their entireties.

TECHNICAL FIELD

The present disclosure is generally related to devices that generate a time-varying magnetic field, and is specifically related to apparatuses, systems, and methods for a compact portable electromagnetic field and ion emitter.

BACKGROUND

Traditional magnetic therapy methods typically involve the use of static magnetic fields produced by permanent magnets incorporated into items such as bracelets, belts, back pads, mattress pads, and mattresses. Although proposed as a noninvasive alternative to pharmacological and nutritional solutions, traditional electromagnetic therapy conducted at higher flux density and/or higher frequency levels can instead sometimes be harmful, while conventional treatments at the lower end of the spectrum can have little to no therapeutic effect without the efforts of medical experts operating the devices. Conventional therapeutic electromagnetic devices are also typically not portable, are more complex, and need relatively skilled medical personnel to operate them effectively. In order to receive treatment using traditional methods, patients must incur the time commitment and expense of traveling to an office where the machine is located during normal business hours. Moreover, some conventional devices permit a relatively wide range of adjustment of field strength and/or frequency, which can lead to ineffective or potentially harmful treatment. There remains a significant need for improved electromagnetic field generator systems, methods, and technologies.

SUMMARY

Apparatuses, systems, and methods for a compact portable electromagnetic field and ion emitter are disclosed. In embodiments, a portable electromagnetic energy generating apparatus includes an electromagnetic energy generating means to produce one or more electromagnetic fields on receipt of at least an electrical signal generated by one or more electrical signal generating means. A clip is connected to the electromagnetic energy generating means through one or more wires. The one or more produced electromagnetic fields are associated with the received electrical signals from a mobile application. The one or more produced electromagnetic fields are adapted to provide a therapeutic effect to an area of a user's body.

In embodiments, a portable electromagnetic energy generating apparatus includes a connecting means for connecting the portable electromagnetic energy generating apparatus with one or more electrical signal generating means to receive electrical signals from the one or more electrical signal generating means at least in a wired communication mode or in a wireless communication mode. The apparatus includes a clip for connecting with the connecting means and an electromagnetic energy generating means to produce one or more electromagnetic fields on receipt of the electrical signals generated by the one or more electrical signal generating means through a mobile application. The one or more produced electromagnetic fields are associated with the received electrical signals.

In embodiments, a method of operating a portable electromagnetic energy generating apparatus includes using a software application and/or a mobile application for controlling the portable electromagnetic energy generating apparatus. Electrical signals are received from one or more electrical signal generating means at least in a wired communication mode or in a wireless communication mode. One or more electromagnetic fields are produced on receipt of the electrical signals generated by the one or more electrical signal generating means using the software application through the mobile application. The one or more produced electromagnetic fields are associated with the received electrical signal.

In embodiments, an apparatus for generating electromagnetic fields includes a torus-shaped mount and a coil including a conducting wire wound around the mount in one of a clockwise configuration or a counterclockwise configuration, such that the coil forms a toroid and has an inductance. The coil is configured to receive electrical signals generated by a user device from amplification of digital audio files stored on the user device. The electrical signals have frequencies in an Extremely Low Frequency (ELF) range and a Very Low Frequency (VLF) range. The coil generates the electromagnetic fields based on the inductance when the electrical signals pass through the coil. The electromagnetic fields include pulsed vortex fields having the frequencies. The electromagnetic fields are configured by the coil to provide therapy to a user proximate to the apparatus. The electromagnetic fields include a left-hand spin torsion field when the wire is wound in the counterclockwise configuration. The electromagnetic fields include a right-hand spin torsion field when the wire is wound in the clockwise configuration. A clip is affixed to the mount at a first end of the clip and encases terminal ends of the wire entering the clip from the coil at the first end of the clip. The clip is shaped and sized to be grasped by a hand of the user and includes a 3.5 mm audio jack disposed at a second end of the clip. The terminal ends of the wire are electrically connected to the 3.5 mm audio jack. The 3.5 mm audio jack is configured to be inserted into a 3.5 mm audio socket of the user device. The clip is configured to pass the electrical signals from the user device to the coil via the 3.5 mm audio jack.

In embodiments, the mount has one or more longitudinal cavities. The apparatus includes one or more gemstones shaped and sized to be embedded in the one or more cavities. The one or more gemstones are configured to generate ions in the presence of the electromagnetic fields. The ions are for providing the therapy to the user.

In embodiments, the mount has a first set of grooves and a second set of grooves crisscrossing the first set of grooves. The coil includes first windings of the wire wound into the first set of grooves of the mount and second windings of the wire wound into the second set of grooves of the mount. The second windings overlay the first windings.

In embodiments, the wire is twisted to increase a resistance of the wire and a density of the electromagnetic fields. The clip is configured to support the mount at the first end and affix the 3.5 mm audio jack at the second end to the user device via the 3.5 mm audio socket.

In embodiments, an apparatus includes a torus-shaped mount and a coil including a conducting wire wound around the mount such that the coil has an inductance. The coil is configured to generate electromagnetic fields based on the inductance when electrical signals pass through the coil. The electromagnetic fields have frequencies in an Extremely Low Frequency (ELF) range and a Very Low Frequency (VLF) range. The electromagnetic fields are to provide therapy to a user. A clip is affixed to the mount and encases terminal ends of the wire. The clip is configured to receive the electrical signals from a user device and pass the electrical signals to the coil via the terminal ends.

In embodiments, the coil forms a toroid. The wire is wound around the mount in one of a clockwise configuration or a counterclockwise configuration.

In embodiments, the electromagnetic fields include a left-hand spin torsion field when the wire is wound in the counterclockwise configuration. The electromagnetic fields include a right-hand spin torsion field when the wire is wound in the clockwise configuration.

In embodiments, the electromagnetic fields include pulsed vortex fields having the frequencies.

In embodiments, the electrical signals are generated by the user device from amplification of digital audio files stored on the user device.

In embodiments, the mount has one or more longitudinal cavities. The apparatus includes one or more gemstones shaped and sized to be embedded in the one or more cavities. The one or more gemstones are configured to generate ions in the presence of the electromagnetic fields. The ions are for providing the therapy to the user.

In embodiments, the mount has a first set of grooves and a second set of grooves crisscrossing the first set of grooves. The coil includes first windings of the wire wound into the first set of grooves of the mount. Second windings of the wire are wound into the second set of grooves of the mount. The second windings overlay the first windings.

In embodiments, the wire is twisted to increase a resistance of the wire and a density of the electromagnetic fields.

In embodiments, the clip is shaped and sized to be grasped by a hand of the user, the clip is affixed to the mount at an end of the clip, and the terminal ends of the wire enter the clip from the coil at the end of the clip.

In embodiments, the clip includes an electrical jack disposed at an end of the clip. The clip is configured to receive the electrical signals from the user device via the electrical jack.

In embodiments, the clip includes an electrical jack electrically coupled to the terminal ends of the wire.

In embodiments, the clip includes an electrical jack configured to be inserted into an electrical socket of the user device for passing the electrical signals from the user device to the apparatus.

In embodiments, the electromagnetic fields include a torsion field having a directional spin. Using the coil in proximity to one or more other coils producing other electromagnetic fields having opposing spins generates a phase-conjugated torsion field.

In embodiments, the clip includes a wireless receiver configured to receive wireless signals generated by a wireless transmitter of the user device. The wireless signals correspond to amplified digital audio files stored on the user device. The electrical signals are generated from the wireless signals.

In embodiments, a method includes amplifying digital audio files stored on a user device of the system. The digital audio files include frequencies in an Extremely Low Frequency (ELF) range and a Very Low Frequency (VLF) range. Electrical signals are generated using the user device based on the amplifying. The electrical signals have the frequencies. The electrical signals are sent to an electrical jack of an apparatus of the system via an electrical socket of the user device. The apparatus is configured to generate electromagnetic fields. The electromagnetic fields are generated using a coil of the system based on an inductance of the coil by passing the electrical signals from the electrical jack through the coil. The electromagnetic fields are configured by the coil to provide therapy to a user proximate to the system.

In embodiments, the electromagnetic fields include pulsed vortex fields having the frequencies.

In embodiments, the coil includes a wire wound in one of a clockwise configuration or a counterclockwise configuration. The electromagnetic fields include a left-hand spin torsion field when the wire is wound in the counterclockwise configuration. The electromagnetic fields include a right-hand spin torsion field when the wire is wound in the clockwise configuration.

BRIEF DESCRIPTION OF THE DRAWINGS

FIG. 14 is a flow diagram illustrating an example process for using a compact portable electromagnetic field and ion apparatus, in accordance with one or more embodiments.

DETAILED DESCRIPTION

Figure 1:
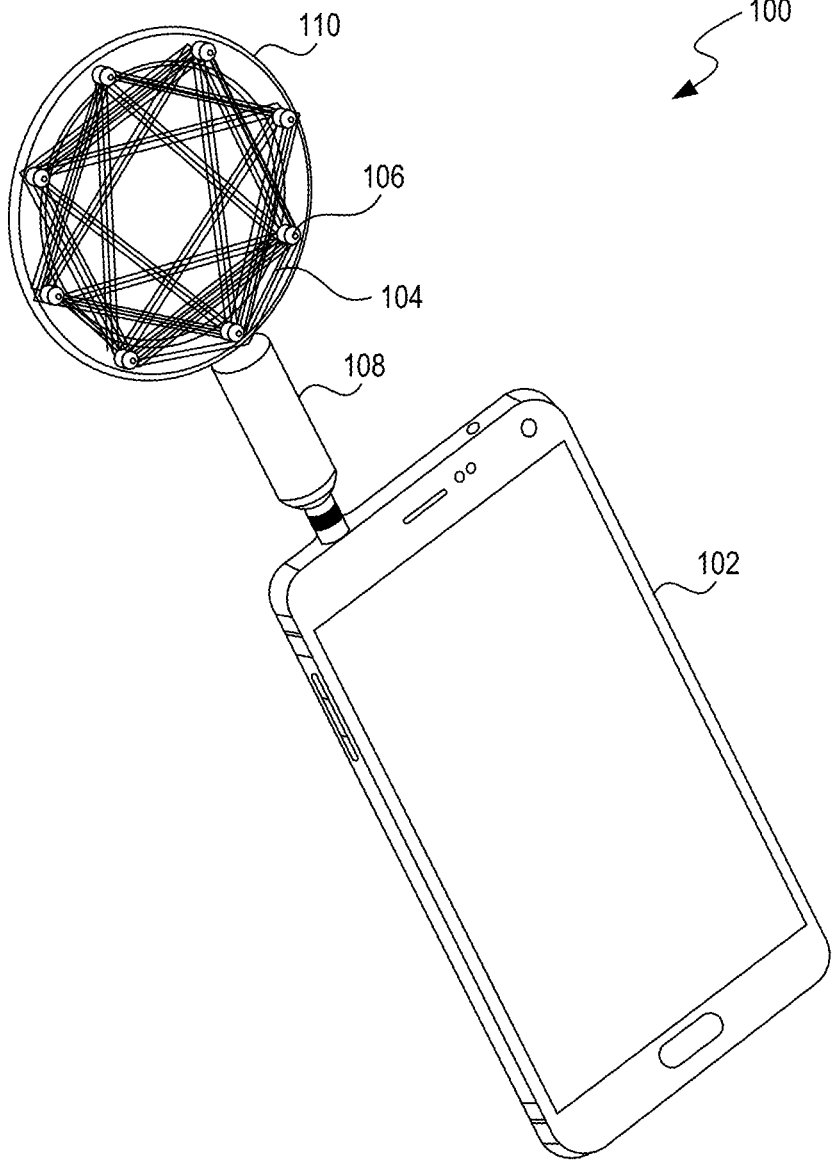
FIG. 1 is a drawing illustrating a perspective view of an example compact portable electromagnetic field and ion emitter apparatus, in accordance with one or more embodiments.

Embodiments of the present disclosure will now be described more thoroughly with reference to the accompanying drawings. Like numerals represent like elements throughout the several figures, in which example embodiments are shown. However, embodiments of the claims can take many different forms and should not be construed as being limited to the embodiments set forth herein. The examples set forth herein are non-limiting examples and are merely examples, among other possible examples.

Throughout this specification, plural instances (e.g., "602") may implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatuses, systems, components, program products, means, or steps for performing a function, and in other ways. These and other aspects, features, and implementations will become apparent from the following descriptions, including the claims.

The embodiments disclosed herein describe a portable electromagnetic energy generating apparatus that includes an electromagnetic energy generating means to produce one or more electromagnetic fields on receipt of at least an electrical signal generated by one or more electrical signal generating means. A clip is connected to the electromagnetic energy generating means through one or more wires. The one or more produced electromagnetic fields are associated with the received electrical signal from a mobile application. The one or more produced electromagnetic fields are adapted to provide a therapeutic effect to an area of a user's body.

In embodiments, an apparatus includes a torus-shaped mount and a coil including a conducting wire wound around the mount such that the coil has an inductance. The coil is configured to generate electromagnetic fields based on the inductance when electrical signals pass through the coil. The electromagnetic fields have frequencies in an Extremely Low Frequency (ELF) range and a Very Low Frequency (VLF) range. The electromagnetic fields are to provide therapy to a user. A clip is affixed to the mount and encases terminal ends of the wire. The clip is configured to receive the electrical signals from a user device and pass the electrical signals to the coil via the terminal ends.

The advantages and benefits of the methods, systems, and apparatus disclosed herein include therapeutic treatment of a wide variety of physical and mental disorders in users by a portable device capable of being operated safely and effectively by the users. The time-varying magnetic fields having a lower frequency and lower flux density generated by the disclosed apparatuses provide more effective therapy than conventional methods. The embodiments disclosed herein can generate electromagnetic fields for therapy from amplified digital frequencies using a consumer-grade user device, such as a smartphone, tablet, laptop, smartwatch, etc., thus reducing cost. The disclosed systems provide methods and apparatuses that do not require skilled personnel to administer. Moreover, in addition to the benefits provided by the frequency coils, the addition of gemstones within the coils has therapeutic benefits (known as piezo-electric or pyro-electric effects) from the additional ions generated from the coils. Some of the more important benefits of the produced ions are that they clear the air of airborne allergens such as pollen, mold spores, bacteria, and viruses. They also clear the air of dust, pet dander, and cigarette smoke.

Further, the implementations disclosed limit the extent of operating adjustments permitted on the part of a patient or practitioner to prevent harm. The apparatuses are capable of treating a wide variety of physical and mental disorders in human or animal subjects and the therapeutic effects achieved are beneficial for brainwaves and cell function. Because the embodiments disclosed include a sound coupling that can be "paired" with a mobile computing device (such as a cell phone, tablet, etc.), users can use a user device software application (app) having an archive of digital therapy sound files to choose from. Embodiments incorporate a stone, such as a gemstone, within the coil to enhance the therapy effectiveness. Moreover, embodiments use a standalone base station to wirelessly send audio content to the apparatus, thus eliminating the need for a mobile computing device.

FIG. 1 is a drawing illustrating a perspective view of an example compact portable electromagnetic field and ion emitter apparatus 100, in accordance with one or more embodiments. Portions of the example compact portable electromagnetic field and ion emitter apparatus 100 and the user device 102 shown in FIG. 1 can be implemented using the example computer system 1500 illustrated and described in more detail with reference to FIG. 15. Likewise, embodiments can include different and/or additional components, or be connected in different ways.

The apparatus 100 includes a coil 104 of bare, insulated, or enameled wire wound on a disc-shaped or donut-shaped mount 110. An example wire (windings 1364) is illustrated and described in more detail with reference to FIG. 13C. The wire is made of a conductive metal, such as copper, and the mount 110 can be made of plastic, wood, or a metal, such as iron. The coil 104 is electrically coupled to the user device 102. The coil 104 functions as an inductor to generate electromagnetic fields from electrical signals provided by the user device 102 for providing therapy to a user. In embodiments, the apparatus 100 incorporates the coil 104 bound in a multi-point pattern, as shown by FIG. 1, and connected to an external amplifier (e.g., within the user device 102 or a wireless amplifier), such that digital audio frequency files are provided to the apparatus 100 by the user device 102. An example amplifier 672 is illustrated and described in more detail with reference to FIG. 6C.

The apparatus 100 can include a sound coupling (e.g., the coil 104) having fixation points 106 arranged in a star-like, toroidal, or cylindrical pattern on the mount 110. The fixation points 106 are sometimes referred to as poles. The fixation points 106 are wound with the wire, and the coil 104 is connected to a digital audio frequency library on the user device 102. In embodiments, the fixation points 106 are circular-shaped bolts. The bolts are made of a rigid metal, such as stainless steel, aluminum, steel, and the like. The bolts are disposed radially at, but not limited to, multiple points around the mount 110 (wheel support). An example digital audio frequency library of audio files 802 is illustrated and described in more detail with reference to FIG. 8. When activated, the audio files are played into an amplifier (e.g., on the user device 102 or an external amplifier) that amplifies the electrical signals and sends the electrical signals to the inductive coil 104, enabling the coil 104 to emit electromagnetic fields for therapy. These digital audio files 802 produce the electromagnetic fields and/or audio frequencies that are emitted through a toroidal wire wound coil.

FIG. 1 shows a perspective view of the apparatus 100 inserted into, affixed to, or plugged into the user device 102. The user device (sometimes referred to as a "user device") can be a smartphone, a tablet, a laptop, a smartwatch, etc. The mount 110 and the coil 104 are connected to an amplifier or to the user device 102 by means of a clip 108 or handle. An example clip 1200 is illustrated and described in more detail with reference to FIG. 12A. In embodiments, one or more stones, such as gemstones, jewels, or the like, are placed in openings, cavities, chambers, or holes in the apparatus 100, such as in the mount 110. An example gemstone 1320 is illustrated and described in more detail with reference to FIG. 13A. An example cavity 1104 in an example mount 1100 is illustrated and described in more detail with reference to FIG. 11.

The clip 108 is connected to the coil 104 and/or the mount 110 and is also connected to the user device 102. The clip 108 can be made of plastic, wood, or a metal, such as powdered iron. In embodiments, a wire that is used to send electrical signals from the user device 102 to the coil 104 passes through the clip 108. In embodiments, the wire has multiple (e.g., 2, 3, 4, etc.) levels of windings around the fixation points 106. The wire and the coil 104 can be connected to an audio input/output device (e.g., user device 102) by means of an electrical jack (e.g., a Lightning audio jack, a micro jack 2.5, a 3.5 mm mini-jack, a 6.3 mm jack, a USB audio jack, a Type-C jack, etc.). An example electrical jack 202 is illustrated and described in more detail with reference to FIG. 2.

Figure 2:
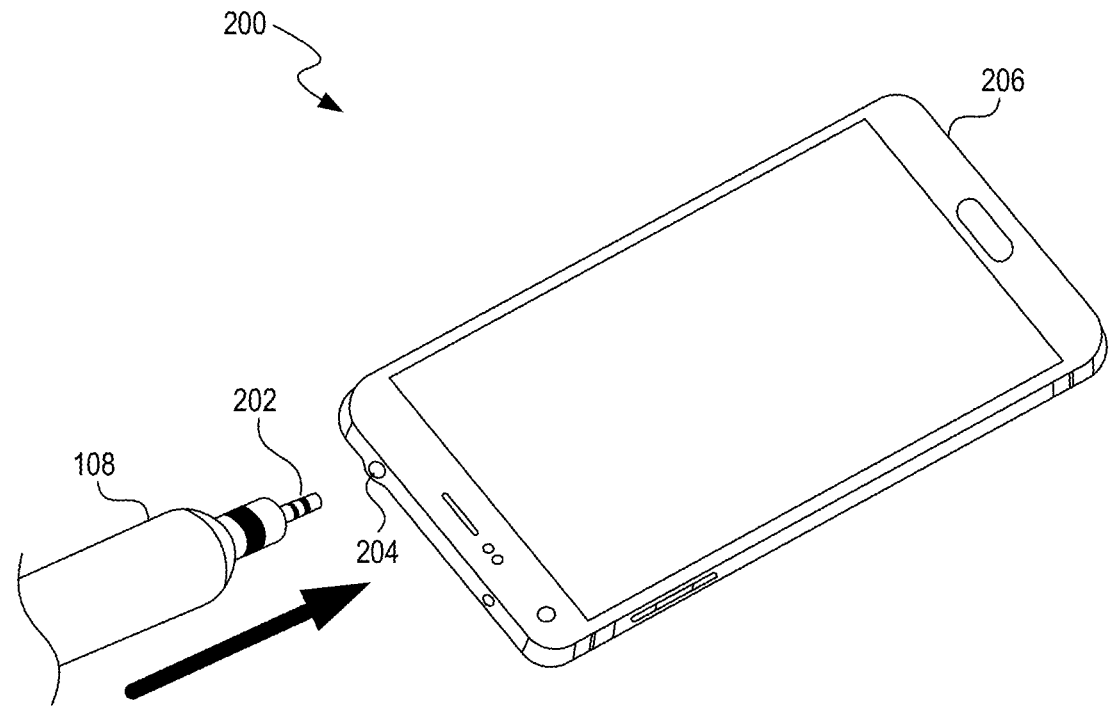
FIG. 2 is a drawing illustrating a perspective view of a portion of an example compact portable electromagnetic field and ion emitter apparatus being attached to a user device, in accordance with one or more embodiments.

FIG. 2 is a drawing illustrating a perspective view of a portion of an example compact portable electromagnetic field and ion emitter apparatus 200 being attached to a user device 206, in accordance with one or more embodiments. Portions of the apparatus 200 and the user device 206 shown in FIG. 2 can be implemented using the example computer system 1500 illustrated and described in more detail with reference to FIG. 15. Likewise, embodiments can include different and/or additional components, or be connected in different ways.

In embodiments, the apparatus 200 receives electrical signals generated by the user device 206 from amplification of digital audio files stored on the user device 206. In embodiments, the user device 206 or apparatus 200 receives digital audio files from a server or the cloud. An example digital audio frequency library of audio files 802 is illustrated and described in more detail with reference to FIG. 8. A clip 108 encases terminal ends of a wire of the apparatus 200 entering the clip 108 from a coil at a first end of the clip 108. An example wire (windings 1364) is illustrated and described in more detail with reference to FIG. 13C. An example coil 502 is illustrated and described in more detail with reference to FIG. 5. An example first end 1204 is illustrated and described in more detail with reference to FIG. 12A.

The clip 108 is shaped and sized to be grasped by a hand of the user. In embodiments, the clip 108 includes an electrical jack 202 disposed at a second end of the clip 108. An example second end 1208 is illustrated and described in more detail with reference to FIG. 12A. The electrical jack can be a Lightning audio jack, a micro jack 2.5, a 3.5 mm mini-jack, a 6.3 mm jack, a USB audio jack, a Type-C jack, etc. The terminal ends of the wire are electrically connected to the electrical jack 202. The electrical jack 202 is configured to be inserted into an electrical socket 204 of the user device 206. The electrical socket 204 corresponds to the electrical jack 202. The clip 108 is configured to pass the electrical signals from the user device 206 to the coil via the electrical jack 202. In embodiments, the clip 108 is configured to support a mount of the apparatus 200 at the first end. An example mount 1100 is illustrated and described in more detail with reference to FIG. 11. In embodiments, the clip 108 is configured to affix the electrical jack 202 at the second end to the user device 206 via the electrical socket 204. In embodiments, the clip 108 is configured to receive the electrical signals from the user device 206 and pass the electrical signals to a coil via the terminal ends of the wire. An example coil 104 is illustrated and described in more detail with reference to FIG. 1.

Figure 3:
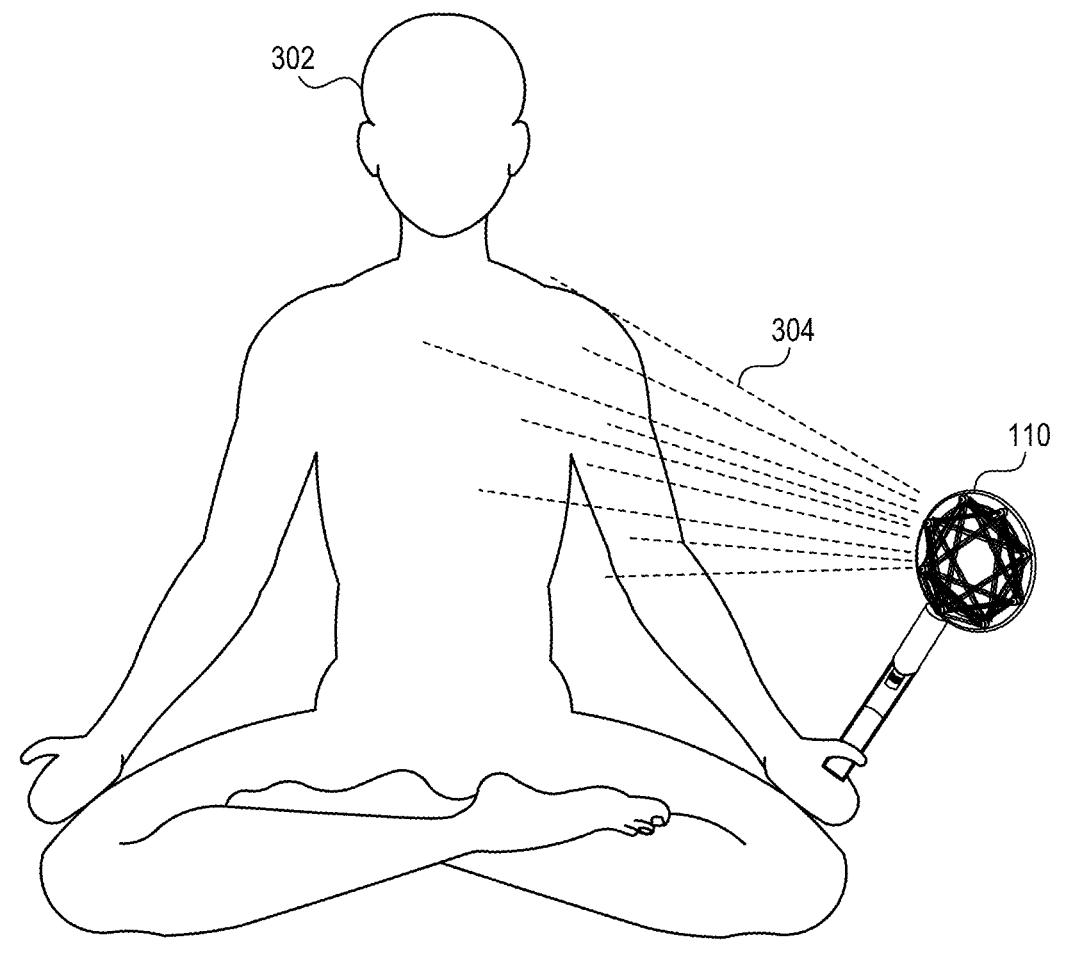
FIG. 3 is a drawing illustrating an example method of using a compact portable electromagnetic field and ion emitter apparatus, in accordance with one or more embodiments.

FIG. 3 is a drawing illustrating an example method of using a compact portable electromagnetic fields 304 and ion emitter apparatus, in accordance with one or more embodiments. The apparatus (having mount 110) is shown plugged into a user device that a user 302 is holding. An example user device 206 is illustrated and described in more detail with reference to FIG. 2. Portions of the apparatus and the user device shown in FIG. 3 can be implemented using the example computer system 1500 illustrated and described in more detail with reference to FIG. 15. Likewise, embodiments can include different and/or additional components, or be connected in different ways.

The apparatus for generating the electromagnetic fields 304 includes the mount 110. In embodiments, the mount 110 has one or more cavities. An example cavity 1008 is illustrated and described in more detail with reference to FIG. 10. The apparatus can include gemstones shaped and sized to be embedded in the one or more cavities. An example gemstone 1320 is illustrated and described in more detail with reference to FIG. 13A. The gemstones are configured to generate ions in the presence of the electromagnetic fields 304. The ions are for providing therapy to the user 302 who is proximate to the apparatus. The apparatus includes a coil including a conducting wire wound around the mount in one of a clockwise configuration or a counterclockwise configuration, such that the coil has an inductance. An example coil 104 is illustrated and described in more detail with reference to FIG. 1. An example wire (windings 1364) is illustrated and described in more detail with reference to FIG. 13C. In embodiments, the coil is configured to receive electrical signals generated by the user device from amplification of digital audio files stored on the user device. In embodiments, the user device receives digital audio files from a server or the cloud. The electrical signals have frequencies in an Extremely Low Frequency (ELF) range and a Very Low Frequency (VLF) range. The ELF range includes electromagnetic radiation (radio waves) having frequencies from 3 hertz (Hz) to 30 Hz, and corresponding wavelengths of 100,000 to 10,000 kilometers (km), respectively. The VLF range includes radio frequencies (RF) in the range of 3-30 kilohertz (kHz), corresponding to wavelengths from 100 to 10 km, respectively. The audio files are converted to electrical signals by the user device or a base station. An example base station 664 is illustrated and described in more detail with reference to FIG. 6C.

The coil generates the electromagnetic fields 304 based on the inductance when the electrical signals pass through the coil. In embodiments, the electromagnetic fields 304 include pulsed vortex fields having the same frequencies. The audio signal frequencies are sent to the copper coil and spin electrons through the copper coil at the speed of light in a circular fashion, creating a pulsed electromagnetic vortex field. The electromagnetic fields 304 are configured by the coil to provide the therapy to the user. A clip is affixed to the mount 110 at a first end of the clip. An example clip 1376 is illustrated and described in more detail with reference to FIG. 13C. The clip encases terminal ends of the wire. In embodiments, the clip includes an electrical jack disposed at a second end of the clip. The terminal ends of the wire are electrically connected to the electrical jack. The clip is configured to pass the electrical signals from the user device to the coil via the electrical jack.

Figure 4:
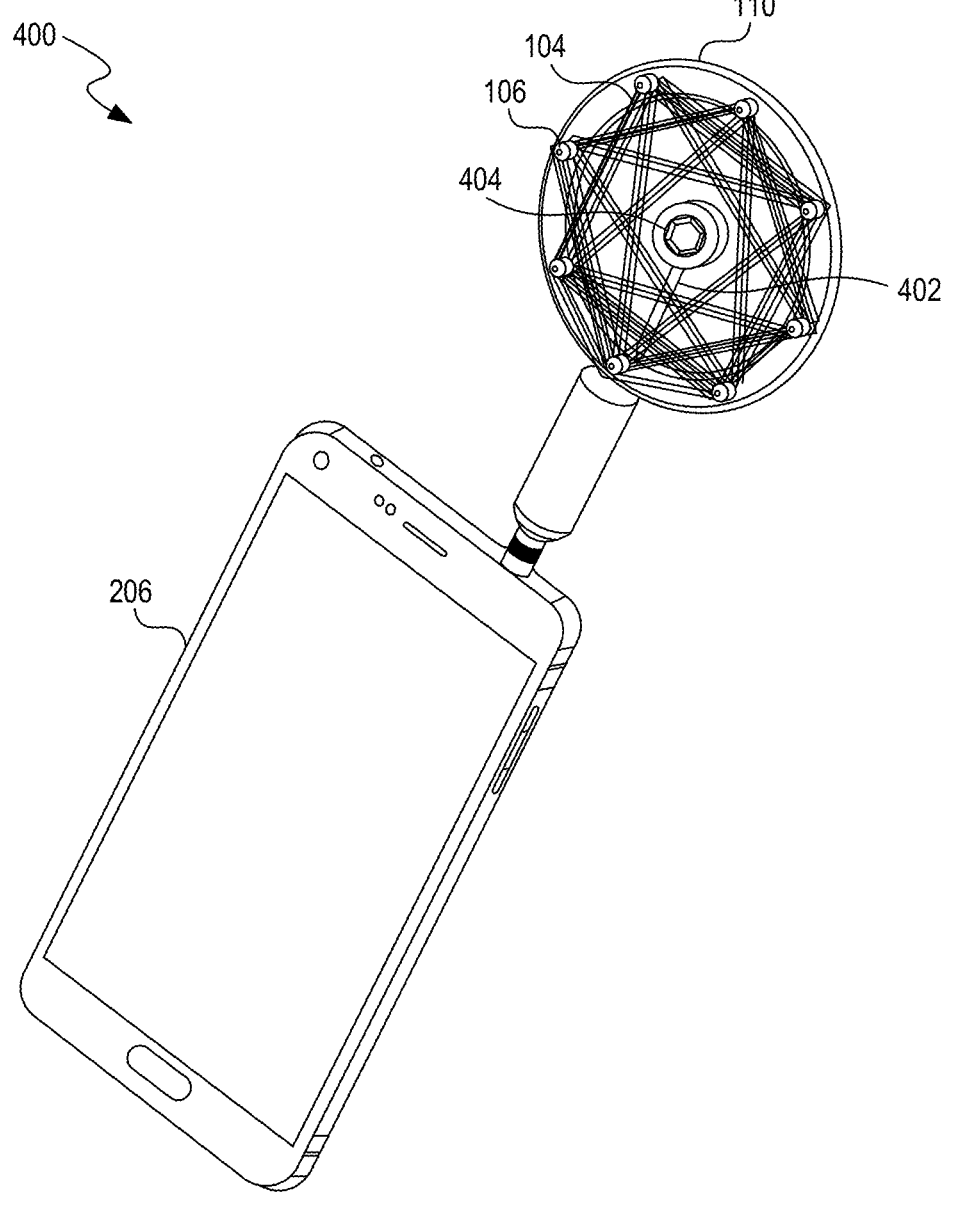
FIG. 4 is a drawing illustrating an example compact portable electromagnetic field and ion emitter apparatus having a stone affixed thereto, in accordance with one or more embodiments.

FIG. 4 is a drawing illustrating an example compact portable electromagnetic field and ion emitter apparatus 400 having a stone 404 affixed thereto, in accordance with one or more embodiments. Portions of the apparatus 400 and the user device 206 shown in FIG. 4 can be implemented using the example computer system 1500 illustrated and described in more detail with reference to FIG. 15. Likewise, embodiments can include different and/or additional components, or be connected in different ways.

The apparatus 400 is for generating electromagnetic fields and includes a wheel-shaped mount 110 having one or more cavities. In embodiments, a gemstone 404 is shaped and sized to be embedded in a cavity and configured to generate ions in the presence of the electromagnetic fields. The ions are for providing therapy to a user proximate to the apparatus 400. The gemstone 404 can be a sapphire, ruby, or quartz, crystal, etc., disposed on the mount 110 and supported by a cross member 402. The apparatus includes a coil 104 including a conducting wire wound around the mount 110 in one of a clockwise configuration or a counterclockwise configuration, such that the coil 104 has an inductance. An example wire (windings 1364) is illustrated and described in more detail with reference to FIG. 13C.

The apparatus 400 can include a sound coupling (e.g., the coil 104) having fixation points 106 arranged in a star-like, toroidal, or cylindrical pattern on the mount 110. The fixation points 106 are sometimes referred to as poles. The fixation points 106 are wound with the wire, and the coil 104 is connected to a digital audio frequency library on the user device 206 by an electrical jack. An example digital audio frequency library of audio files 802 is illustrated and described in more detail with reference to FIG. 8. When activated, the audio files are played into an amplifier (e.g., on the user device 206 or an external amplifier) that amplifies the electrical signals and sends the electrical signals to the inductive coil 104, enabling the coil 104 to emit electromagnetic fields for therapy.

In embodiments, the coil 104 is configured to receive the electrical signals generated by the user device 206 from amplification of the digital audio files stored on the user device 206. In embodiments, the user device 206 receives digital audio files from a server or the cloud. The electrical signals have frequencies in an Extremely Low Frequency (ELF) range and a Very Low Frequency (VLF) range. The coil 104 generates the electromagnetic fields based on the inductance when the electrical signals pass through the coil 104. In embodiments, the electromagnetic fields include pulsed vortex fields having the ELF/VLF frequencies. The electromagnetic fields are configured by the coil 104 to provide the therapy to the user.

Figure 5:
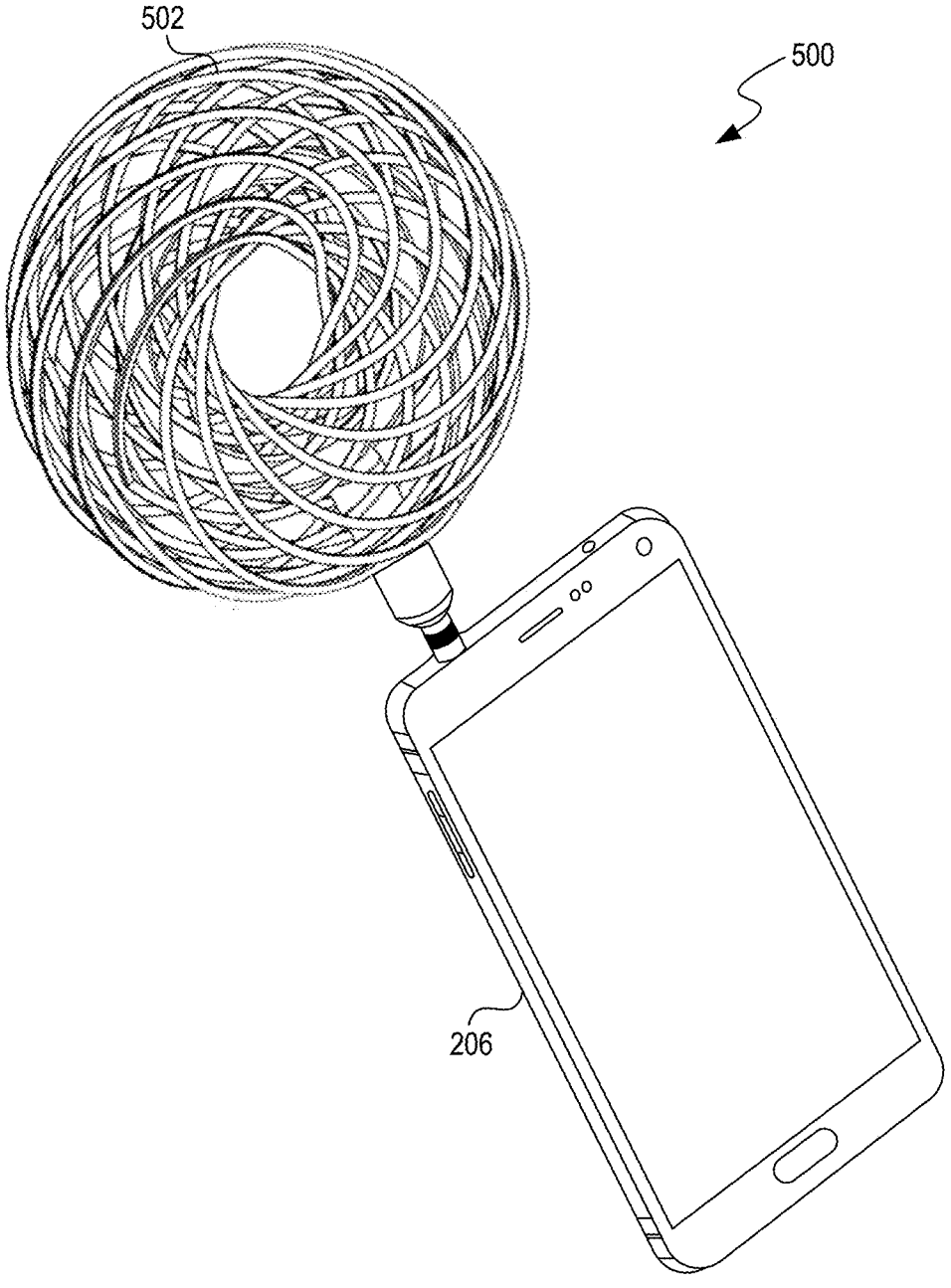
FIG. 5 is a drawing illustrating an example compact portable electromagnetic field and ion emitter apparatus having a coil, in accordance with one or more embodiments.

FIG. 5 is a drawing illustrating an example compact portable electromagnetic field and ion emitter apparatus 500 having a coil 502, in accordance with one or more embodiments. Portions of the apparatus 500 and the user device 206 shown in FIG. 5 can be implemented using the example computer system 1500 illustrated and described in more detail with reference to FIG. 15. Likewise, embodiments can include different and/or additional components, or be connected in different ways.

The apparatus 500 includes the coil 502 of bare, insulated, or enameled wire wound on a circular, ring-shaped, spherical, disc-shaped, or donut-shaped mount. An example mount 900 is illustrated and described in more detail with reference to FIG. 9. An example wire (windings 1364) is illustrated and described in more detail with reference to FIG. 13C. The wire is made of a conductive metal, such as copper, and the mount can be made of plastic, wood, or a metal, such as powdered iron. The coil 502 is electrically coupled to the user device 206. The coil 502 functions as an inductor to generate an electromagnetic field from electrical signals provided by the user device 206 for providing therapy to a user.

In embodiments, the apparatus 500 is powered by a power supply electrically coupled to a circuit (e.g., within a user device 206) that produces an AC or DC output, which is transmitted to the inductive coil 502 in the apparatus 500. For example, the inductive coil 502 can include a number of wire windings wrapped about the mount (e.g., a body having an open or air center, or, alternatively, a ferrous core). In response to the electrical signals output from the circuit, electromagnetic fields are generated by the coil 502 that can be directed toward the area(s) of the body of a user or patient to be treated. For example, the apparatus 500 is operated using a digital audio frequency library on the user device 206. An example digital audio frequency library of audio files 802 is illustrated and described in more detail with reference to FIG. 8. When an application on the user device 206 is activated, audio files are played into an amplifier (e.g., on the user device 206 or on the apparatus 500), through which the electrical signals are amplified and sent to the coil 502, allowing it to emit electromagnetic fields. An example amplifier 672 is illustrated and described in more detail with reference to FIG. 6C.

In embodiments, the user device 206 produces a pulsed or time-varying electrical output having a square wave, a sine wave, a triangular wave, or the like. Such electrical output can be at essentially any selected frequency and voltage. For example, a pulsed output from the user device 206 can result in the generation of a time-varying or pulsed magnetic field by the coil 502. If the user device 206 or other external circuit driving the apparatus 500 emits an AC signal, the position of the north and south poles of the resulting magnetic field from the coil 502 changes with each cycle, whereas a DC electrical signal generates an electromagnetic field in which the position of the magnetic poles remains constant.

Figure 6A:
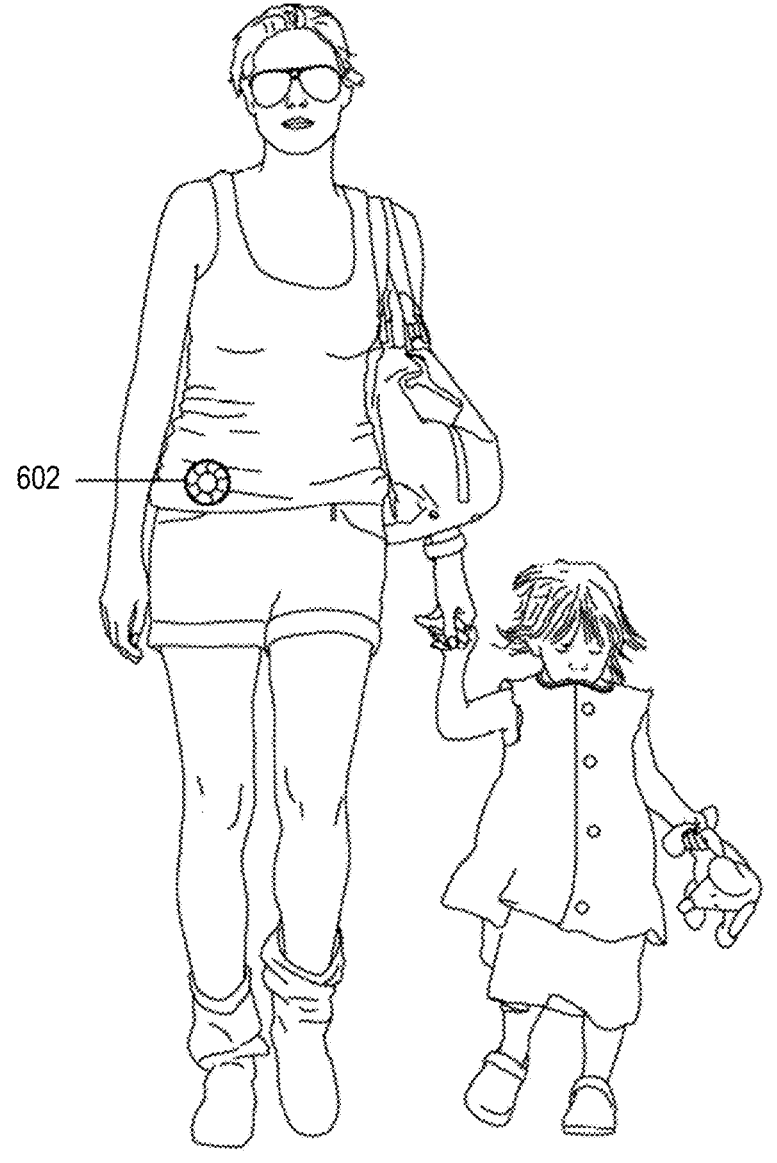
FIG. 6A is a drawing illustrating an example method of using a compact portable electromagnetic field and ion emitter apparatus, in accordance with one or more embodiments.

FIG. 6A is a drawing illustrating an example method of using a compact portable electromagnetic field and ion emitter apparatus 602, in accordance with one or more embodiments. The apparatus 602 is hung on, fastened to, or clipped to clothing of a user. The apparatus 602 is portable and powered by a battery. Hence, the user can use the apparatus 602 while moving, walking, sitting, etc. In embodiments, the apparatus 602 is plugged into a user device that is on the user's person or in a bag of the user. An example user device 206 is illustrated and described in more detail with reference to FIG. 2. For example, an electrical jack in a clip of the apparatus 602 can be plugged into an electrical socket of the user device. An example electrical jack 202, example clip 108, and example electrical socket 204 are illustrated and described in more detail with reference to FIG. 2.

In another example, a wire, cord, or connecting cable of the apparatus 602 is plugged into a user device that is on the user's person or in a bag of the user. An example cable 1392 is illustrated and described in more detail with reference to FIG. 13C. One end of the cable is electrically coupled to terminal ends of a wire of a coil of the apparatus 602 (e.g., encased by a clip of the apparatus 602). An example coil 104 is illustrated and described in more detail with reference to FIG. 1. An example wire (windings 1364) is illustrated and described in more detail with reference to FIG. 13C. Another end distal to the one end is electrically coupled to an electrical jack. The electrical jack is inserted into an electrical socket of the user device.

In embodiments, the apparatus 602 is wirelessly connected to the user device or to a base station. An example base station 664 is illustrated and described in more detail with reference to FIG. 6C. For example, the user device or base station can have a wireless transmitter that transmits the electrical signals (audio signals) to a wireless receiver of the apparatus 602. An example transmitter 692 is illustrated and described in more detail with reference to FIG. 6C. An example wireless receiver 688 is illustrated and described in more detail with reference to FIG. 6C. The apparatus 602 can have a built-in amplifier to amplify the received signals before generating the electromagnetic fields. An example amplifier 1384 is illustrated and described in more detail with reference to FIG. 13C. The signals can be wirelessly transmitted using Bluetooth, Wi-Fi, etc.

Figure 6B:
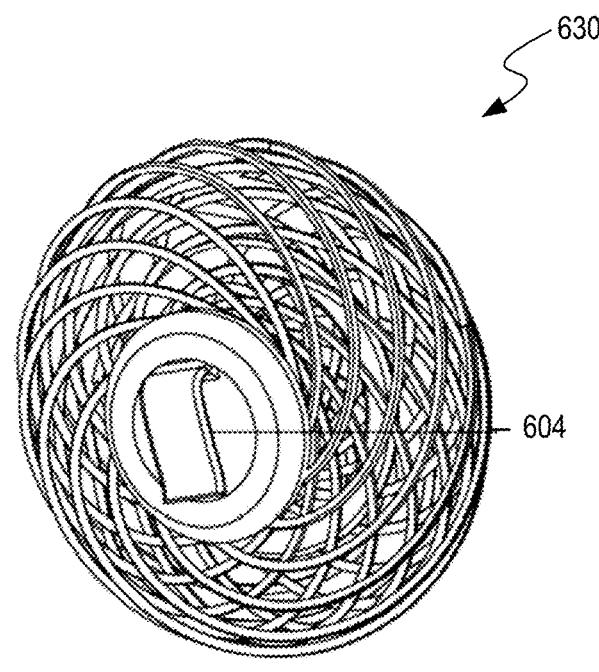
FIG. 6B is a drawing illustrating an example compact portable electromagnetic field and ion emitter apparatus, in accordance with one or more embodiments.

FIG. 6B is a drawing illustrating an example compact portable electromagnetic field and ion emitter apparatus 630, in accordance with one or more embodiments. The apparatus 630 can be hung on, fastened to, or clipped to clothing of a user using a clip 604. Hence, the user can use the apparatus 630 while moving, walking, sitting, etc.

Figure 6C:
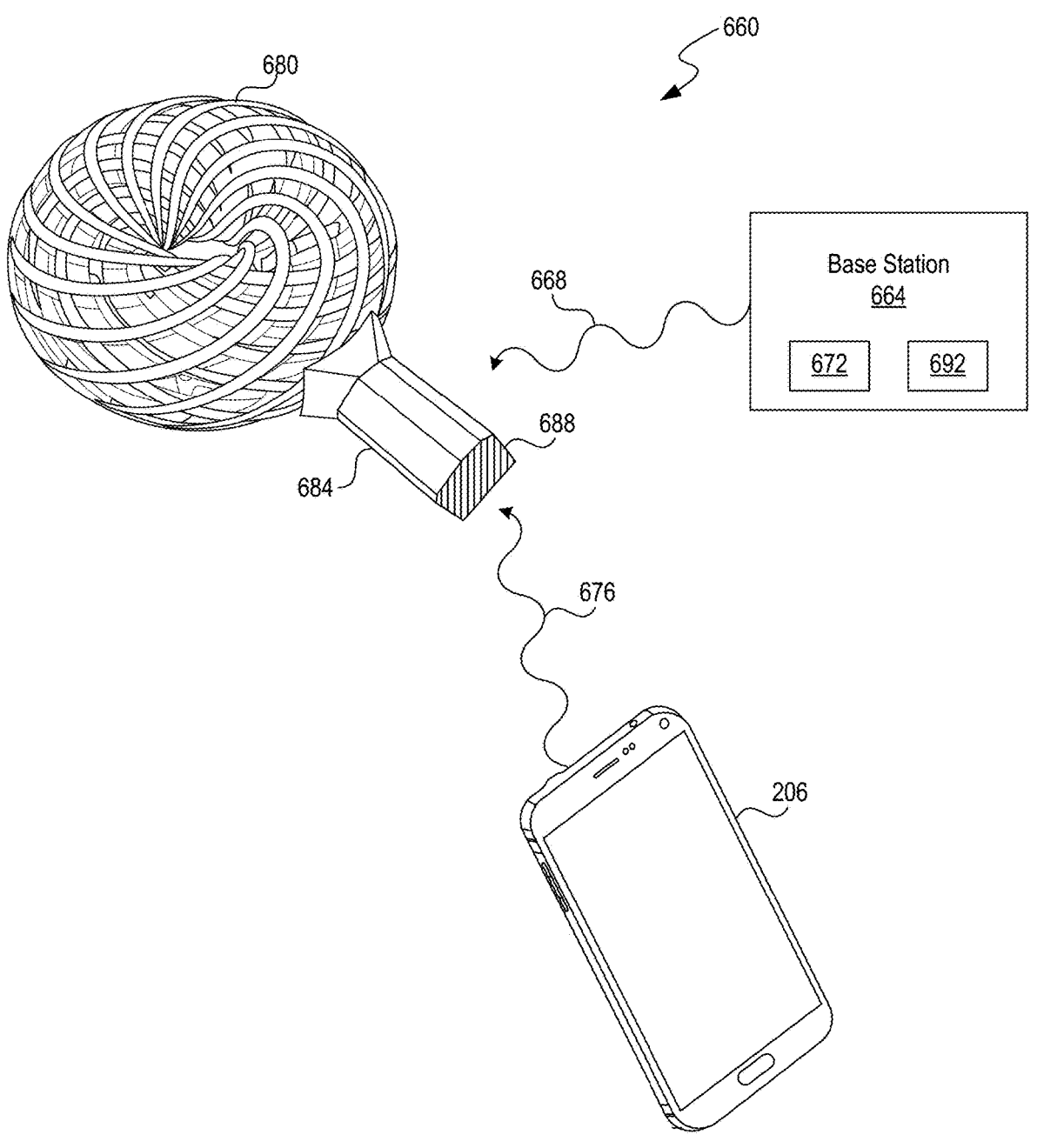
FIG. 6C is a drawing illustrating an example system for emitting electromagnetic fields and ions, in accordance with one or more embodiments.

FIG. 6C is a drawing illustrating an example system 660 for emitting electromagnetic fields and ions, in accordance with one or more embodiments. The system 660 includes an apparatus 680, a base station 664, and a user device 206. Portions of the system 660 shown in FIG. 6C can be implemented using the example computer system 1500 illustrated and described in more detail with reference to FIG. 15. Likewise, embodiments can include different and/or additional components, or be connected in different ways.

The apparatus 680 includes a torus-shaped mount. An example mount 900 is illustrated and described in more detail with reference to FIG. 9. The apparatus 680 includes a coil including a conducting wire wound around the mount, such that the coil has an inductance. An example coil 104 is illustrated and described in more detail with reference to FIG. 1. An example wire (windings 1364) is illustrated and described in more detail with reference to FIG. 13C. The coil is configured to generate electromagnetic fields based on the inductance when electrical signals 668 pass through the coil. The time-varying magnetic fields have lower frequencies and lower flux densities effective in the treatment of a wide variety of physical and mental disorders. The electrical signals 668 are generated by a base station 664 and wirelessly transmitted to the apparatus 680. Other electrical signals 676 can be generated by the user device 206 and wirelessly transmitted to the apparatus 680. The electromagnetic fields have frequencies in an Extremely Low Frequency (ELF) range and a Very Low Frequency (VLF) range. The electromagnetic fields provide therapy to a user.

The apparatus 680 can have a clip 684 affixed to the mount and encasing terminal ends of the wire. The clip 684 is configured to receive the electrical signals 676 from the user device 206 and pass the electrical signals 676 to the coil via the terminal ends. In embodiments, the coil forms a toroid, and the wire is wound around the mount in one of a clockwise configuration or a counterclockwise configuration. In embodiments, the generated electromagnetic fields include a left-hand spin torsion field when the wire is wound in the counterclockwise configuration. The electromagnetic fields include a right-hand spin torsion field when the wire is wound in the clockwise configuration.

In embodiments, the clip 684 has a wireless receiver 688 embedded into, located within, or otherwise communicably coupled to the coil. The wireless receiver 688 receives the electrical signals 676 and/or the electrical signals 668 wirelessly and passes the electrical signals 676 to the coil via the terminal ends. The terminal ends are electrically coupled to the wireless receiver 688 to receive the electrical signals from the wireless receiver 688 and send them to the coil. The wireless receiver 688 can receive radio or microwave signals in electromagnetic waves transmitted through space, and inducing an electrical current in a receiving antenna. The wireless receiver 688 detects and demodulates the current to recreate the information sent by a transmitter. The wireless receiver 688 can use optical communication technology based on light propagating in free space to receive wireless data.

The user device 206 is illustrated and described in more detail with reference to FIG. 1. The base station 664 is an electrical or computer device that stores digital audio files or receives digital audio files from a server or the cloud. In embodiments, the base station 664 includes a transceiver connecting a number of other devices (e.g., apparatus 680, user device 206) to one another and/or to a wider area. The base station 664 can also act as a switch for apparatuses 680 in a network or connect them to the Internet. The base station 664 can play digital audio files to convert them to audio signals (wireless electrical signals 668). In embodiments, the base station 664 includes an amplifier 672 and a transmitter 692. The amplifier 672 amplifies audio signals and the transmitter 692 wirelessly transmits the electrical signals 668 to the apparatus 680.

Figure 7:
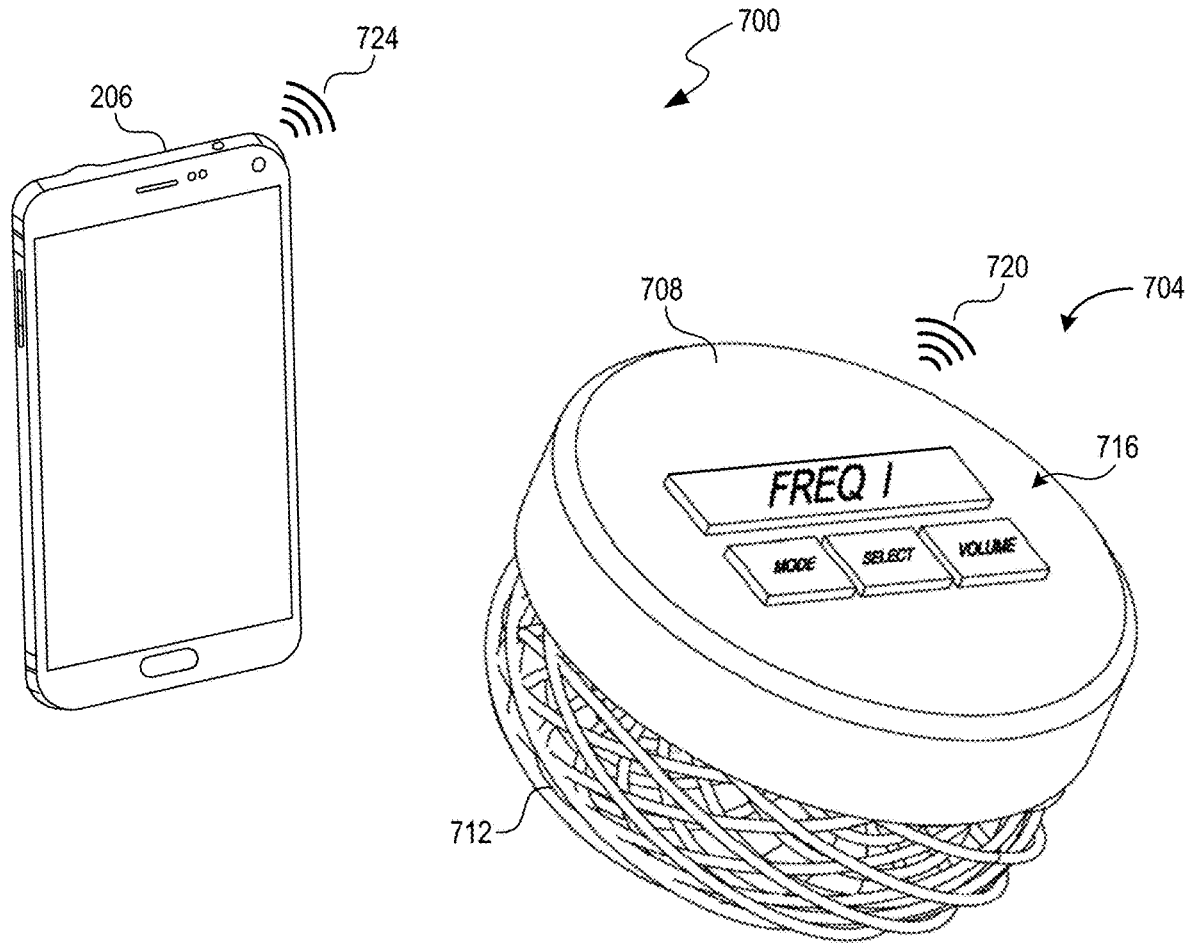
FIG. 7 is a drawing illustrating a user device transmitting content to an example compact portable electromagnetic field and ion emitter apparatus, in accordance with one or more embodiments.

FIG. 7 is a drawing illustrating a user device 206 transmitting content to an example compact portable electromagnetic field and ion emitter apparatus 704, in accordance with one or more embodiments. The user device 206 is illustrated and described in more detail with reference to FIG. 2. The system 700 illustrated includes the user device 206 and the apparatus 704. Portions of the system 700 shown in FIG. 7 can be implemented using the example computer system 1500 illustrated and described in more detail with reference to FIG. 15. Likewise, embodiments can include different and/or additional components, or be connected in different ways.

The apparatus 704 includes a coil 712 made of a conducting wire wound around a mount in one of a clockwise configuration or a counterclockwise configuration, such that the coil 712 has an inductance. An example mount 900 is illustrated and described in more detail with reference to FIG. 9. An example wire (windings 1364) is illustrated and described in more detail with reference to FIG. 13C. The user device 206 transmits wireless audio signals 720, 724, which are received by a receiver of the apparatus 704. An example wireless receiver 1388 is illustrated and described in more detail with reference to FIG. 13C. The apparatus 704 has a base 708. The base 708 can be made of plastic, wood, or a metal, such as powdered iron. The base 708 is attached to the mount and encases terminal ends of the wire. The terminal ends of the wire are connected to the receiver and/or an amplifier inside the apparatus 704. The apparatus 704 is configured to pass the electrical signals 720, 724 from the user device 206 to the coil. The buttons 716 embedded in the base 708 can be used by a user to control the volume, mode, and frequencies of the electromagnetic fields and ions emitted for providing therapy to the user.

Figure 8:
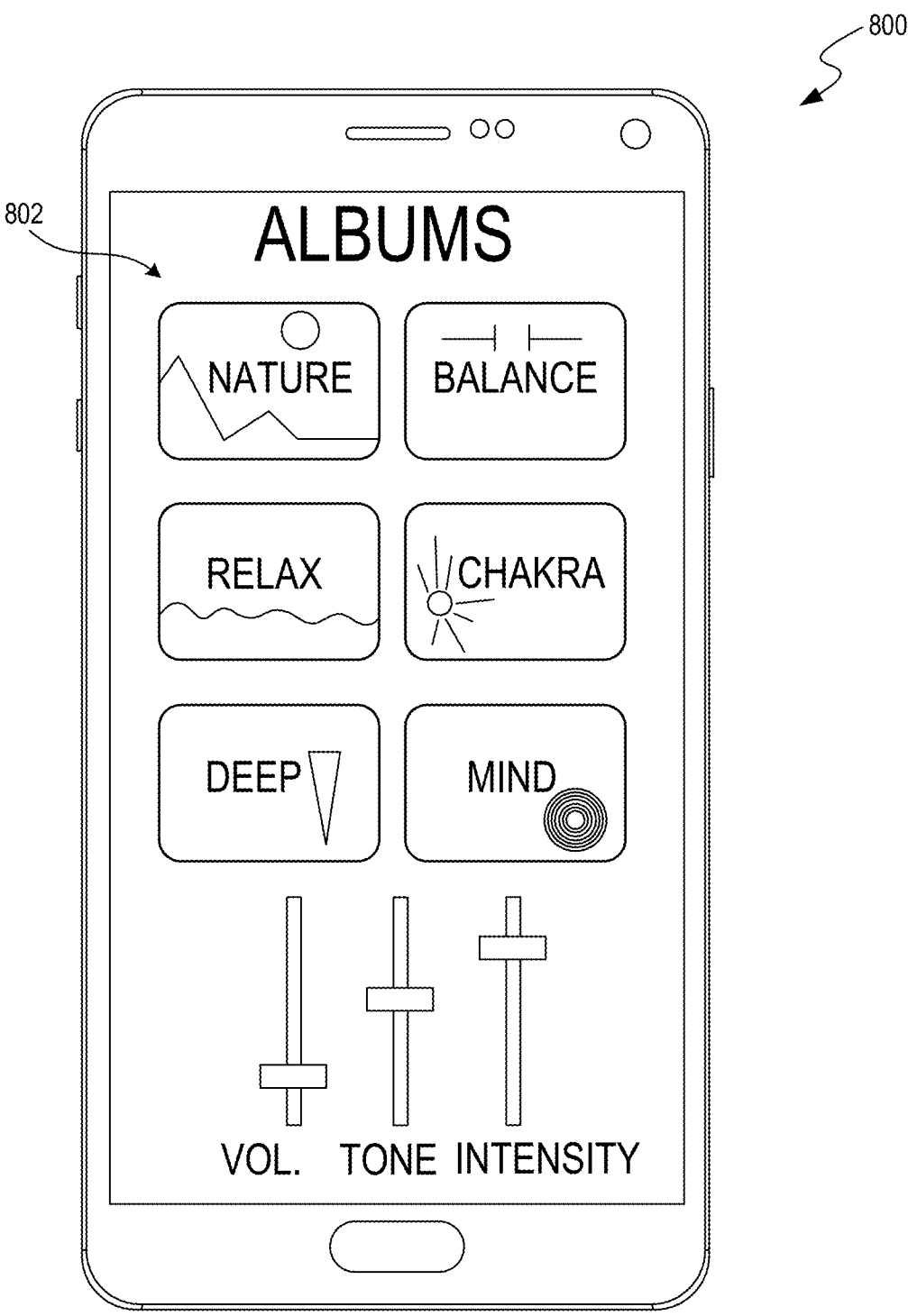
FIG. 8 is a drawing illustrating an example user device for transmitting content to an example compact portable electromagnetic field and ion emitter apparatus, in accordance with one or more embodiments.

FIG. 8 is a drawing illustrating an example user device 800 for transmitting content to a compact portable electromagnetic field and ion emitter apparatus, in accordance with one or more embodiments. The content refers to audio/electrical signals. The user device 800 is similar to the user device 102 illustrated and described in more detail with reference to FIG. 1. The user device 800 can be implemented using the example computer system 1500 illustrated and described in more detail with reference to FIG. 15. Likewise, embodiments can include different and/or additional components, or be connected in different ways.

In embodiments, the user device 800 generates electrical signals from amplification of digital audio files 802 stored on the user device 800. In embodiments, the user device 800 receives the digital audio files 802 from a server or the cloud. The audio files 802 and electrical signals have frequencies in an Extremely Low Frequency (ELF) range and a Very Low Frequency (VLF) range. In embodiments, the frequencies used are in the ranges 0.1-22000 Hz for therapeutic effects. A portable electromagnetic field generator (toroidal coil) produces a unique toroidal field. The toroidal coil winding (yin or yang) clockwise or counterclockwise moves electrons in opposite directions.

In embodiments, the operation of the user device 800 is controlled by a software application compatible with different operating systems and/or a mobile application running on different mobile operating systems to produce the electromagnetic fields and/or audio frequencies that are emitted through a toroidal wire wound coil. The application can be utilized to control the coil power and frequencies. The application can be used by a user on a smartphone and/or computing device.

In embodiments, a mobile application is operated on the user device 800 that has sound file selections that allow users to determine which types of audio frequencies are transmitted to a coil. The audio files include multiple "Life Force" frequencies associated with mitigating a multitude of maladies such as, but not limited to, allergies, emotional issues, chronic illnesses, etc. The frequencies used may include 1 Hz to 30,000 Hz at a multitude of incremental frequencies, or preset and/or harmonic frequencies that play multiple frequencies at the same time. An app having multiple setting options, such as audio volume, tone, or intensity, can be used. The software application can include functions such as, but not limited to, selecting a digital file or controlling digital file intensity, volume, frequency, tone, and the like. The software can be written from code that includes Java, C++, Microsoft® Visual Basic®, Fortran, Basic, and the like. The software can be compatible with multiple operating systems, such as Microsoft® Windows®, Apple®, or Android™, and can be compatible with multiple hardware platforms, such as personal desktops, laptops, tablets, smartphones, and the like.

Figure 9:
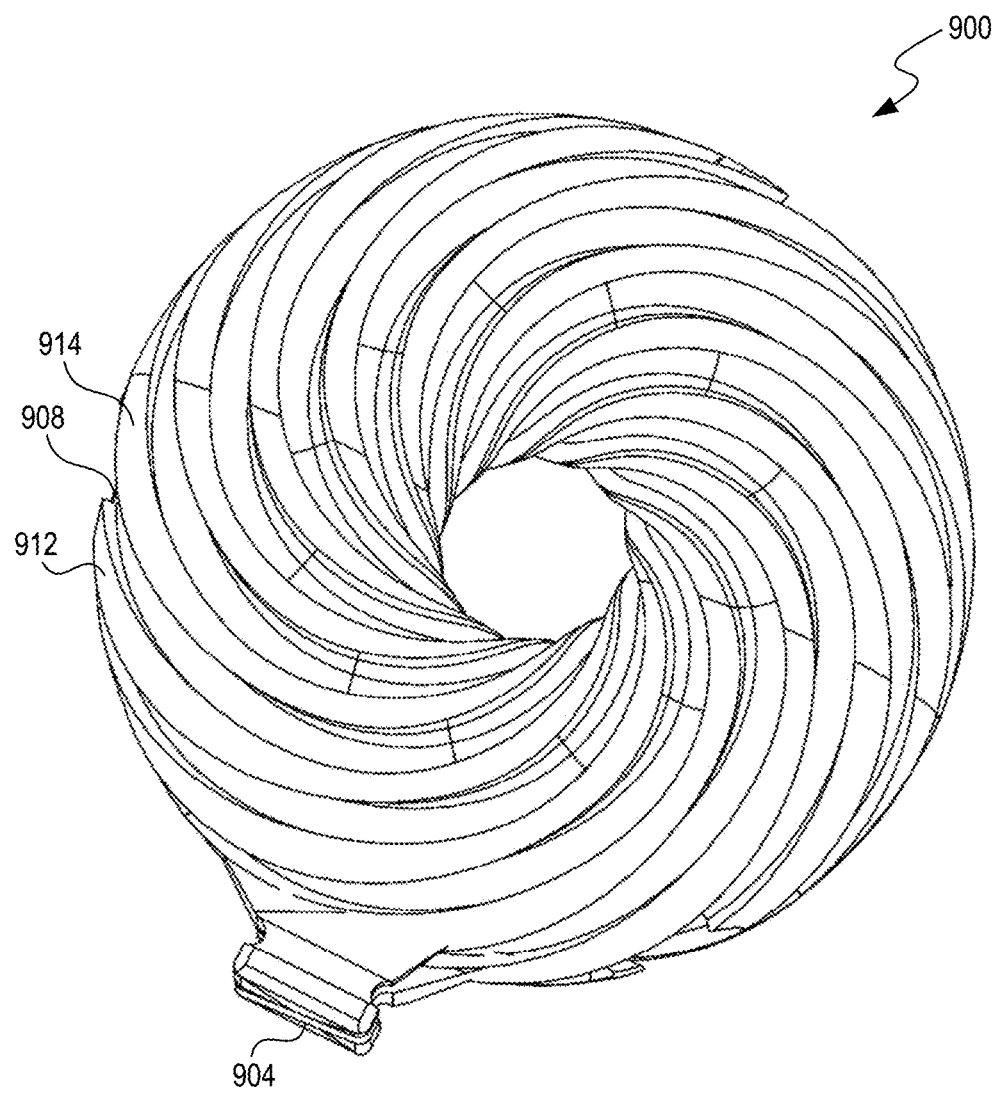
FIG. 9 is a drawing illustrating an example mount for a compact portable electromagnetic field and ion emitter apparatus, in accordance with one or more embodiments.

FIG. 9 is a drawing illustrating an example mount 900 for a compact portable electromagnetic field and ion emitter apparatus, in accordance with one or more embodiments. An example apparatus 1360 is illustrated and described in more detail with reference to FIG. 13C. The apparatus is used for generating electromagnetic fields. In embodiments, the mount 900 is a torus-shaped mount. The mount 900 can be made of plastic, wood, or a metal, such as iron. In embodiments, the mount 900 can have an open or air center, or, alternatively, a ferrous core.

In embodiments, the mount 900 has a first set of grooves 908. Each groove 908 lies between two ridges 912, 914. The mount can have a second set of grooves crisscrossing the first set of grooves 908. The apparatus includes a coil including first windings of a wire wound into the first set of grooves 908 of the mount 900. An example coil 502 is illustrated and described in more detail with reference to FIG. 5. Example first windings 1368 are illustrated and described in more detail with reference to FIG. 13C. The coil can include second windings of the wire wound into the second set of grooves of the mount 900. Example second windings 1364 are illustrated and described in more detail with reference to FIG. 13C. The second windings overlay the first windings (see FIG. 13C). In embodiments, the wire has multiple (e.g., 2, 3, 4, etc.) levels of windings.

The end 904 of the mount 900 is shaped and sized to fit into or be inserted into a first end of a clip. An example clip 1200 having a first end 1204 is illustrated and described in more detail with reference to FIG. 12A. For example, the handle or clip receives the toroid's distal ends 904. The clip or handle fits the distal end 904 of the toroid with wire exiting the other end of the clip. The distal end 904 of the toroid is locked in the clip.

Figure 10:
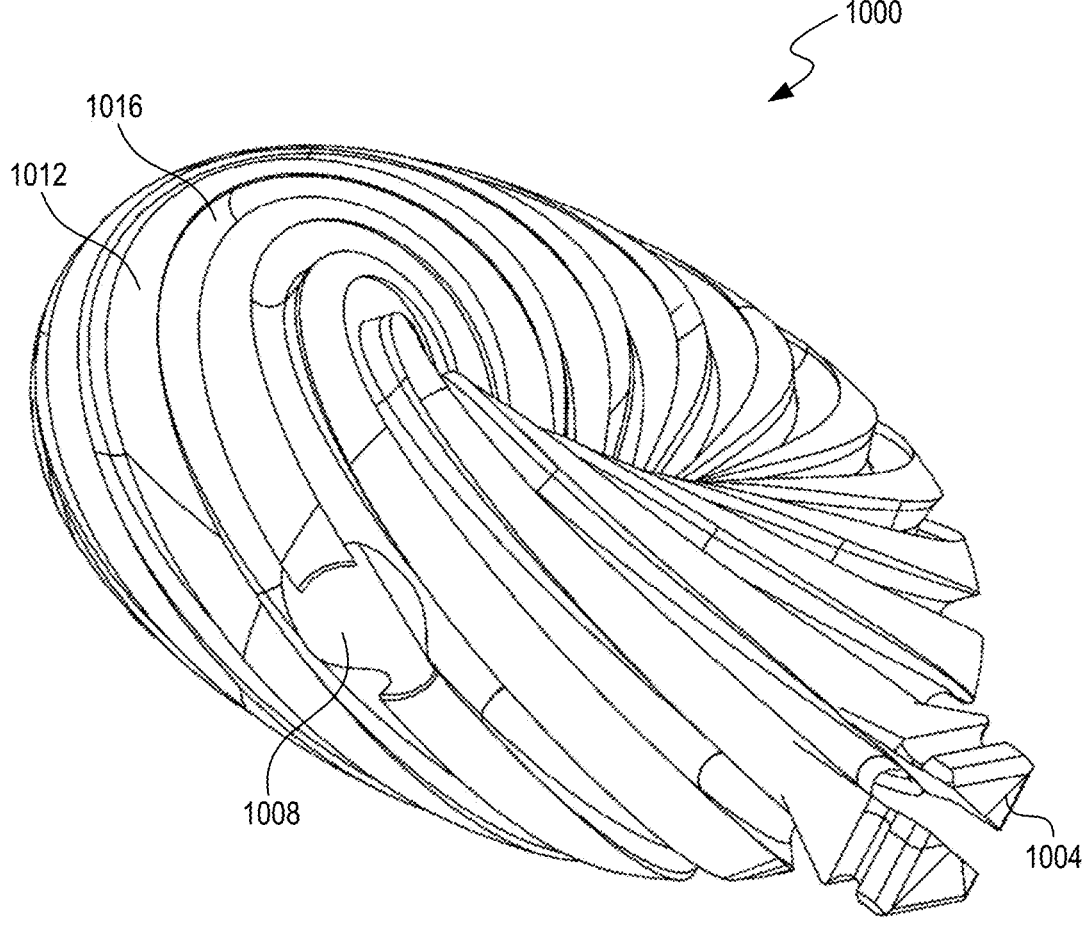
FIG. 10 is a drawing illustrating an example mount for a compact portable electromagnetic field and ion emitter apparatus, in accordance with one or more embodiments.

FIG. 10 is a drawing illustrating an example mount 1000 for a compact portable electromagnetic field and ion emitter apparatus, in accordance with one or more embodiments. An example apparatus 1360 is illustrated and described in more detail with reference to FIG. 13C. The apparatus is used for generating electromagnetic fields. In embodiments, the mount 1000 is a torus-shaped mount. The mount 1000 can be made of plastic, wood, or a metal, such as iron. In embodiments, the mount 1000 can have an open or air center, or, alternatively, a ferrous core.

In embodiments, the mount 1000 has a set of grooves 1016. Each groove 1016 lies between two ridges. An example ridge 1012 is shown by FIG. 10. The apparatus includes a coil including windings of a wire wound into the set of grooves 1016 of the mount 1000. An example coil 502 is illustrated and described in more detail with reference to FIG. 5. Example windings 1368 are illustrated and described in more detail with reference to FIG. 13C. In embodiments, the mount 1000 has one or more longitudinal cavities. A mouth 1008 of a cavity is shown by FIG. 10. The end 1004 of the mount 1000 is shaped and sized to fit into or be inserted into a first end of a clip. An example clip 1200 having a first end 1204 is illustrated and described in more detail with reference to FIG. 12A.

Figure 11:
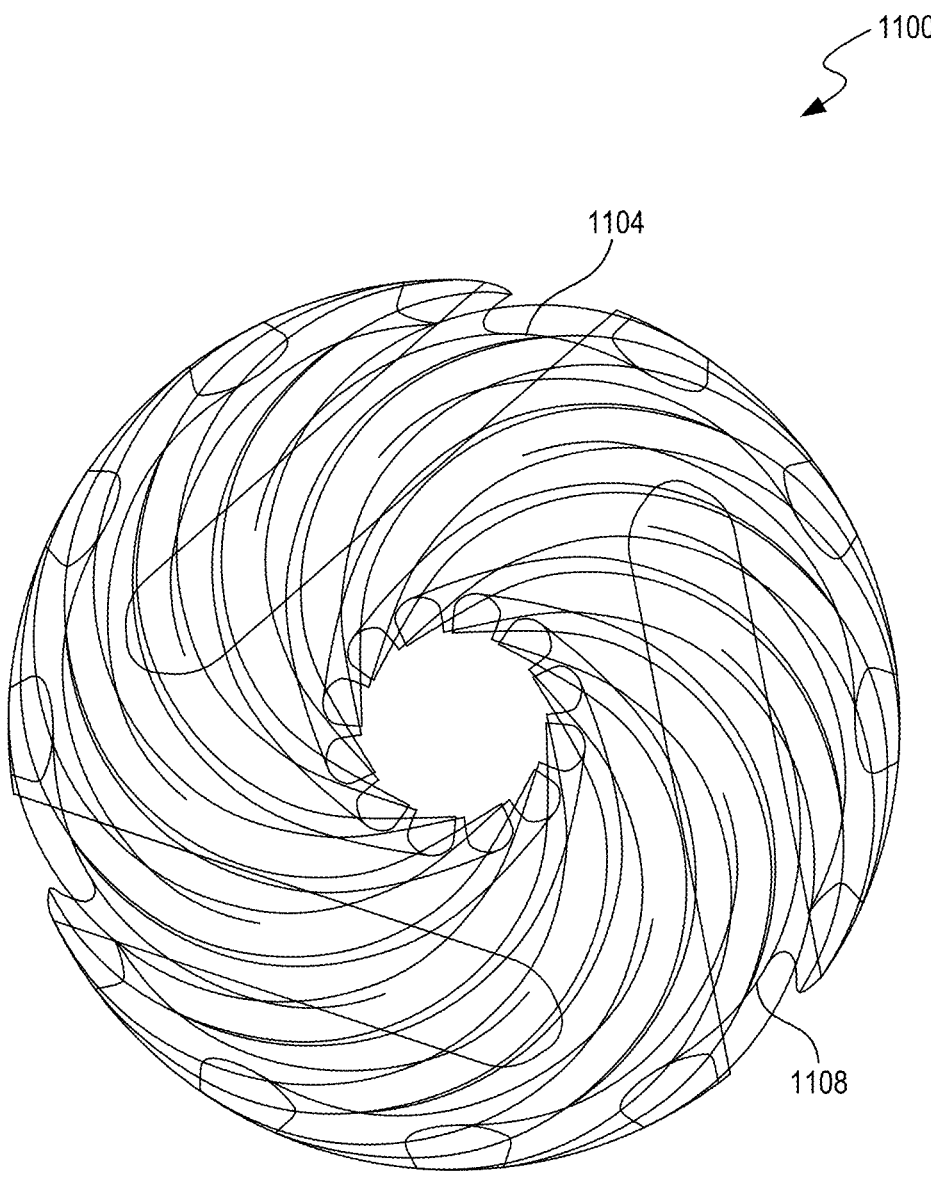
FIG. 11 is a drawing illustrating an example mount for a compact portable electromagnetic field and ion emitter apparatus, in accordance with one or more embodiments.

FIG. 11 is a drawing illustrating an example mount 1100 for a compact portable electromagnetic field and ion emitter apparatus, in accordance with one or more embodiments. An example apparatus 1360 is illustrated and described in more detail with reference to FIG. 13C. The apparatus is used for generating electromagnetic fields. In embodiments, the mount 1100 is a torus-shaped mount. The mount 1100 can be made of plastic, wood, or a metal, such as iron. In embodiments, the mount 1100 can have an open or air center, or, alternatively, a ferrous core.

In embodiments, the mount 1100 has longitudinal cavities 1104, 1108. Gemstones are shaped and sized to be embedded in the cavities 1104, 1108. An example gemstone 1320 is illustrated and described in more detail with reference to FIG. 13A. The gemstones are configured to generate ions in the presence of the electromagnetic fields. The ions are for providing therapy to a user proximate to the apparatus.

Figure 12A:
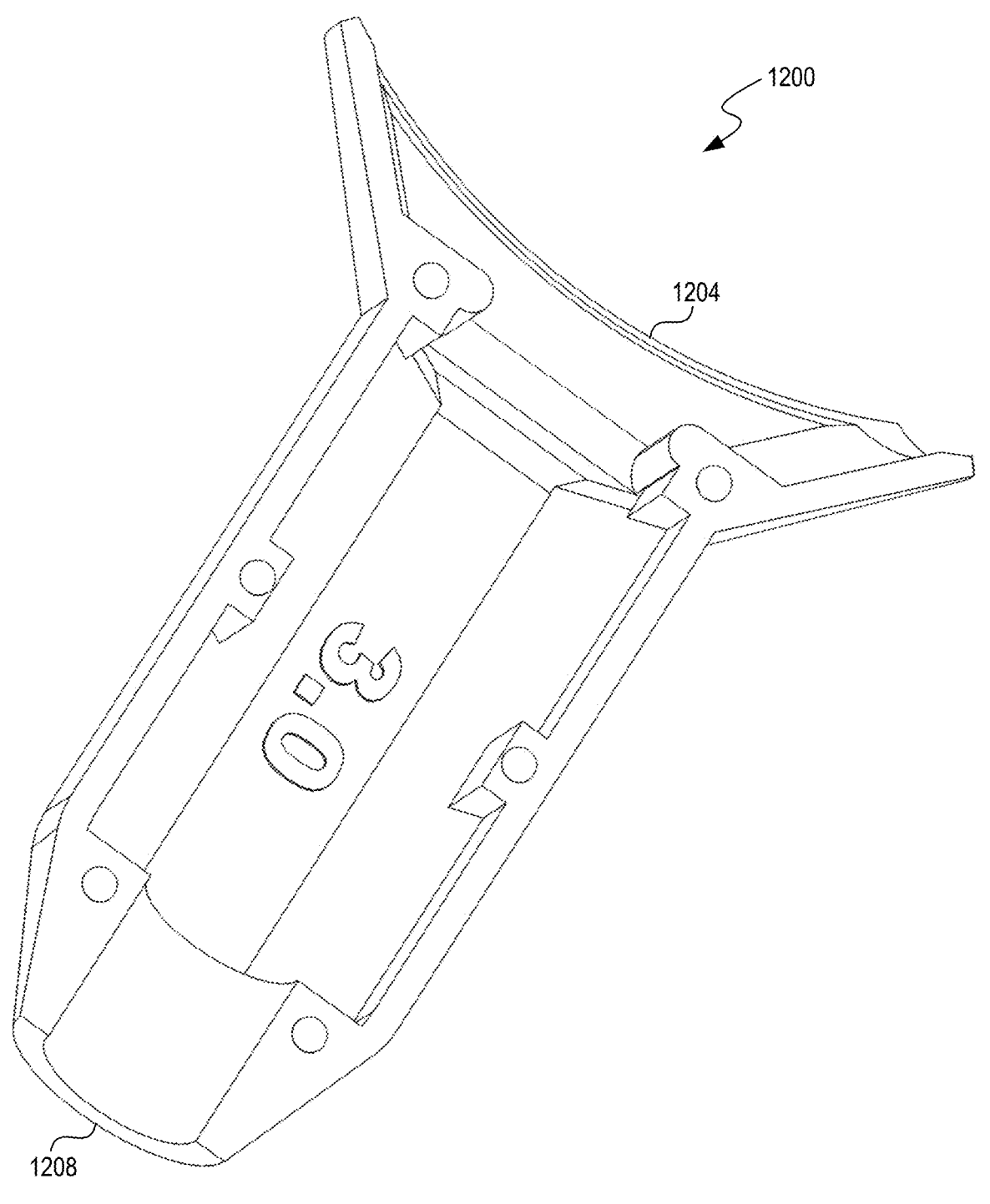
FIG. 12A is a drawing illustrating an inner surface of a portion of an example clip for a compact portable electromagnetic field and ion emitter apparatus, in accordance with one or more embodiments.

FIG. 12A is a drawing illustrating an inner surface of a portion of an example clip 1200 for a compact portable electromagnetic field and ion emitter apparatus, in accordance with one or more embodiments. An example apparatus 1360 is illustrated and described in more detail with reference to FIG. 13C. The apparatus is used for generating electromagnetic fields.

Figure 12B:
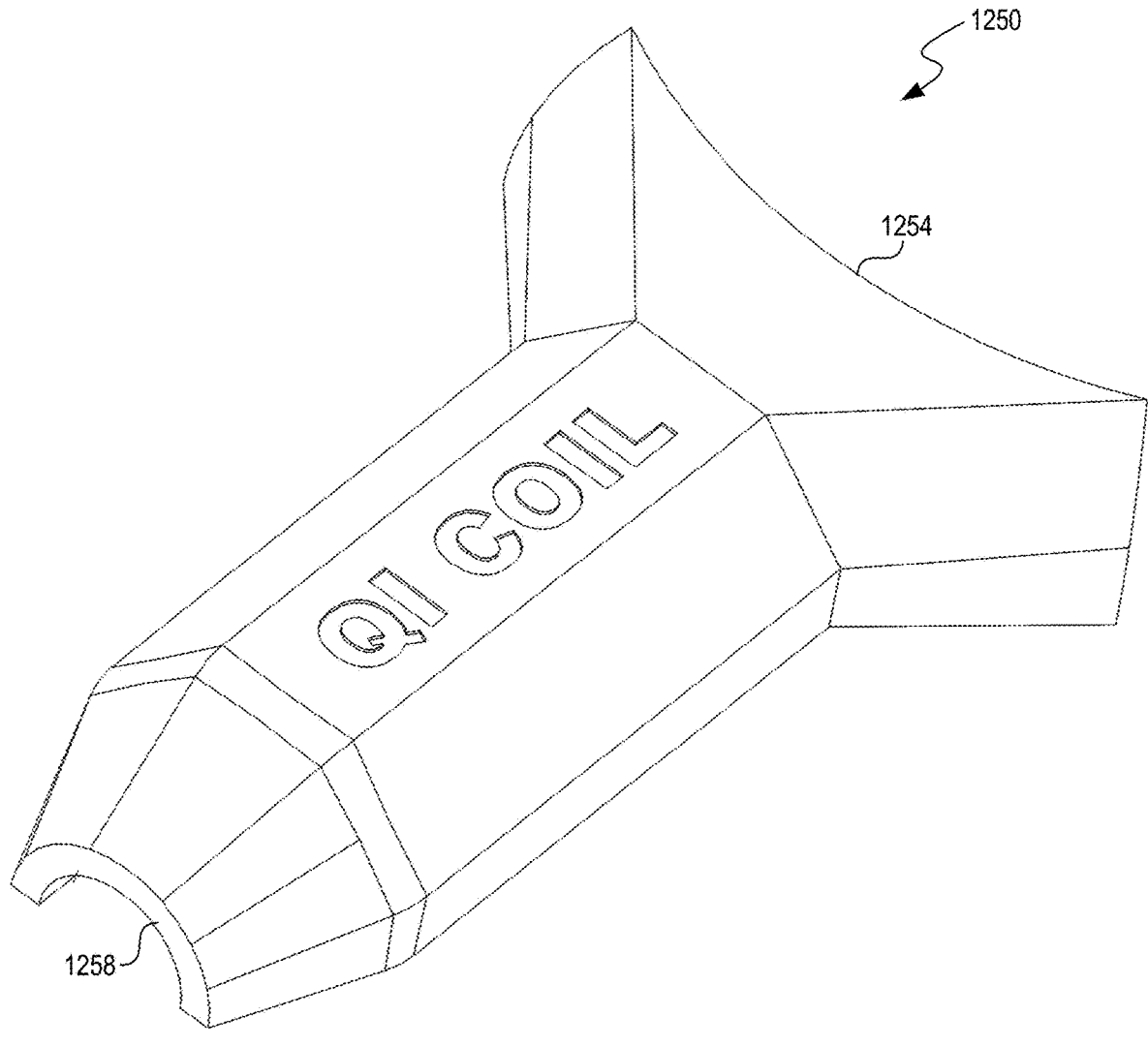
FIG. 12B is a drawing illustrating an outer surface of a portion of an example clip for a compact portable electromagnetic field and ion emitter apparatus, in accordance with one or more embodiments.

In embodiments, the clip 1200 is affixed to a mount of the apparatus at a first end 1204 of the clip 1200. An example mount 900 is illustrated and described in more detail with reference to FIG. 9. The clip 1200 can be tubular in shape or prism-shaped and the first end 1204 can be flared or widened to accommodate an end of the mount. A portion of the clip can be shaped like a hexagonal or octagonal prism as shown by FIGS. 12A-12B. An example end 904 of a mount is illustrated and described in more detail with reference to FIG. 9. In embodiments, the clip 1200 encases terminal ends of a wire of the apparatus. An example wire (windings 1364) is illustrated and described in more detail with reference to FIG. 13C.

In embodiments, the clip includes or encloses an electrical jack (e.g., 3.5 mm audio jack) disposed at a second end 1208 of the clip 1200. An example electrical jack 202 is illustrated and described in more detail with reference to FIG. 2. The second end 1208 can be narrowed or tapered as shown by FIG. 12A to secure the electrical jack or secure a cable exiting the clip as shown by FIG. 13C. An example cable 1392 is illustrated and described in more detail with reference to FIG. 13C. In embodiments, the terminal ends of the wire are electrically connected to the electrical jack. The clip 1200 is configured to pass the electrical signals from a user device 206 to a coil via the electrical jack and/or cable. An example user device 206 is illustrated and described in more detail with reference to FIG. 2. An example coil 502 is illustrated and described in more detail with reference to FIG. 5. The clip 1200 is shaped and sized to be grasped by a hand of a user. The electrical jack is configured to be inserted into an electrical socket of the user device to receive the electrical signals. An example electrical socket 204 is illustrated and described in more detail with reference to FIG. 2. The terminal ends of the wire enter the clip 1200 from the coil at the first end 1204 of the clip 1200.

FIG. 12B is a drawing illustrating an outer surface of a portion of an example clip 1250 for a compact portable electromagnetic field and ion emitter apparatus, in accordance with one or more embodiments. An example apparatus 1360 is illustrated and described in more detail with reference to FIG. 13C. The apparatus is used for generating electromagnetic fields. The clip 1250 is shaped and sized to be grasped by a hand of a user for holding and carrying the apparatus. The clip 1250 is affixed to a mount of the apparatus at an end 1254 of the clip 1250. An example mount 900 is illustrated and described in more detail with reference to FIG. 9. Terminal ends of a wire of the apparatus enter the clip 1250 from a coil of the apparatus at the end 1254 of the clip 1250. An example wire (windings 1364) is illustrated and described in more detail with reference to FIG. 13C. An example coil 502 is illustrated and described in more detail with reference to FIG. 5.

In embodiments, the clip 1250 includes an electrical jack disposed at an end 1258 of the clip 1250. An example electrical jack 202 is illustrated and described in more detail with reference to FIG. 2. The clip 1250 is configured to receive the electrical signals from a user device 206 via the electrical jack. An example user device 206 is illustrated and described in more detail with reference to FIG. 2. In embodiments, the electrical jack is electrically coupled (e.g., soldered) to the terminal ends of the wire. In embodiments, the electrical jack is configured to be inserted into an electrical socket of the user device for passing the electrical signals from the user device to the apparatus. An example electrical socket 204 is illustrated and described in more detail with reference to FIG. 2.

In embodiments, the wire is twisted to increase a resistance of the wire and a density of the electromagnetic fields generated. The inductance and density of the electromagnetic fields generated are described in more detail with reference to FIG. 13C. In embodiments, the clip 1250 is configured to support the mount at the end 1254 and affix the electrical jack at the end 1258 to the user device via an electrical socket.

Figure 13A:
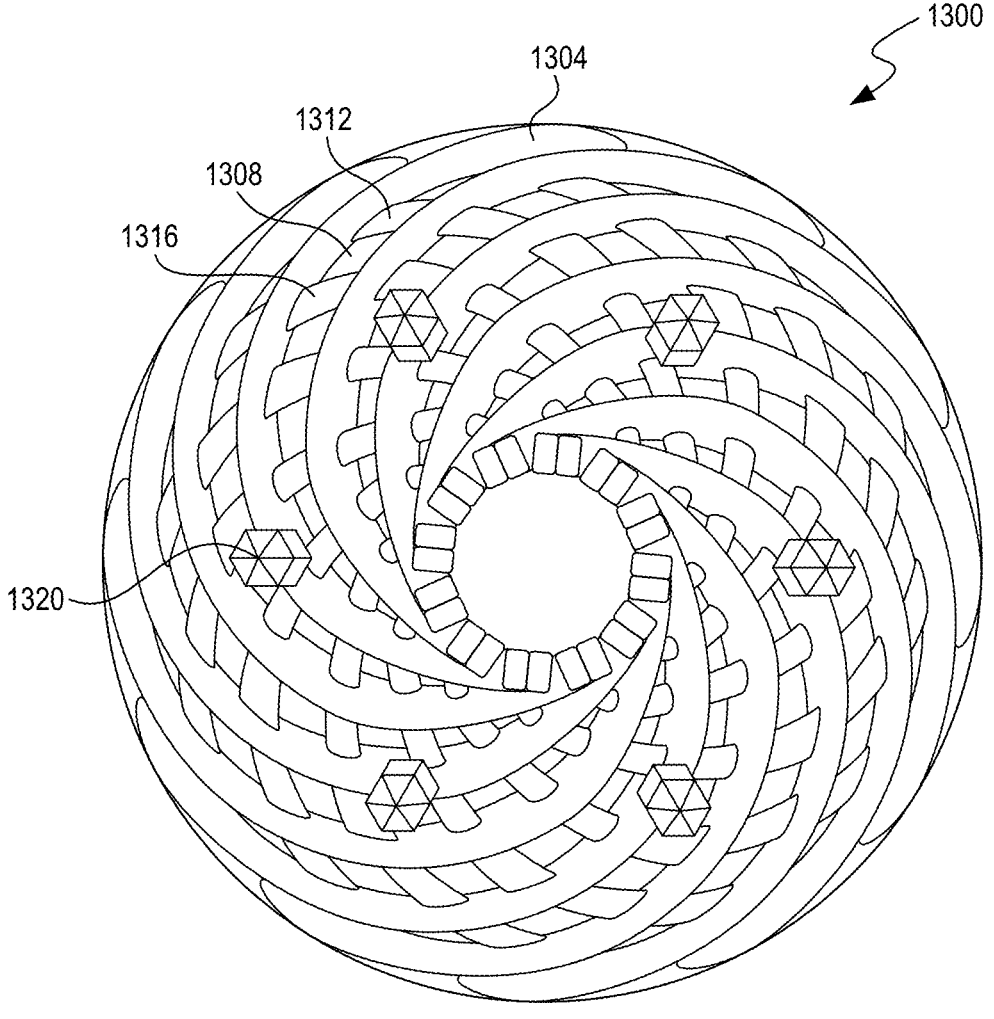
FIG. 13A is a drawing illustrating an example mount for a compact portable electromagnetic field and ion emitter apparatus, in accordance with one or more embodiments.

FIG. 13A is a drawing illustrating an example mount 1300 for a compact portable electromagnetic field and ion emitter apparatus, in accordance with one or more embodiments. An example apparatus 1360 is illustrated and described in more detail with reference to FIG. 13C. The apparatus is used for generating electromagnetic fields.

In embodiments, the mount 1300 has a first set 1304 of grooves and a second set 1308 of grooves crisscrossing the first set 1304 of grooves. A coil of the apparatus includes first windings of a wire wound into the first set 1304 of grooves of the mount 1300. An example coil and first windings 1368 are illustrated and described in more detail with reference to FIG. 13C. The coil includes second windings of the wire wound into the second set 1308 of grooves of the mount 1300. Example second windings 1364 are illustrated and described in more detail with reference to FIG. 13C. Each groove of the second set 1308 lies between two ridges 1312, 1316. Each groove of the first set 1304 also lies between two ridges as shown by FIG. 13A. The second windings overlay the first windings.

Gemstones 1320 are shaped and sized to be embedded in one or more cavities. Example cavities 1104, 1108 are illustrated and described in more detail with reference to FIG. 11. The gemstones 1320 are configured to generate ions in the presence of the electromagnetic fields. The ions are for providing therapy to a user proximate to the apparatus. For example, the addition of gemstones 1320 within the coil can have therapeutic benefits (known as piezoelectric or pyro-electric effects) when additional ions are generated using the coil. Some of the more important benefits of ions are that they clear the air of airborne allergens, such as pollen, mold spores, bacteria, or viruses. The ions also clear the air of dust, pet dander, and cigarette smoke.

Figure 13B:
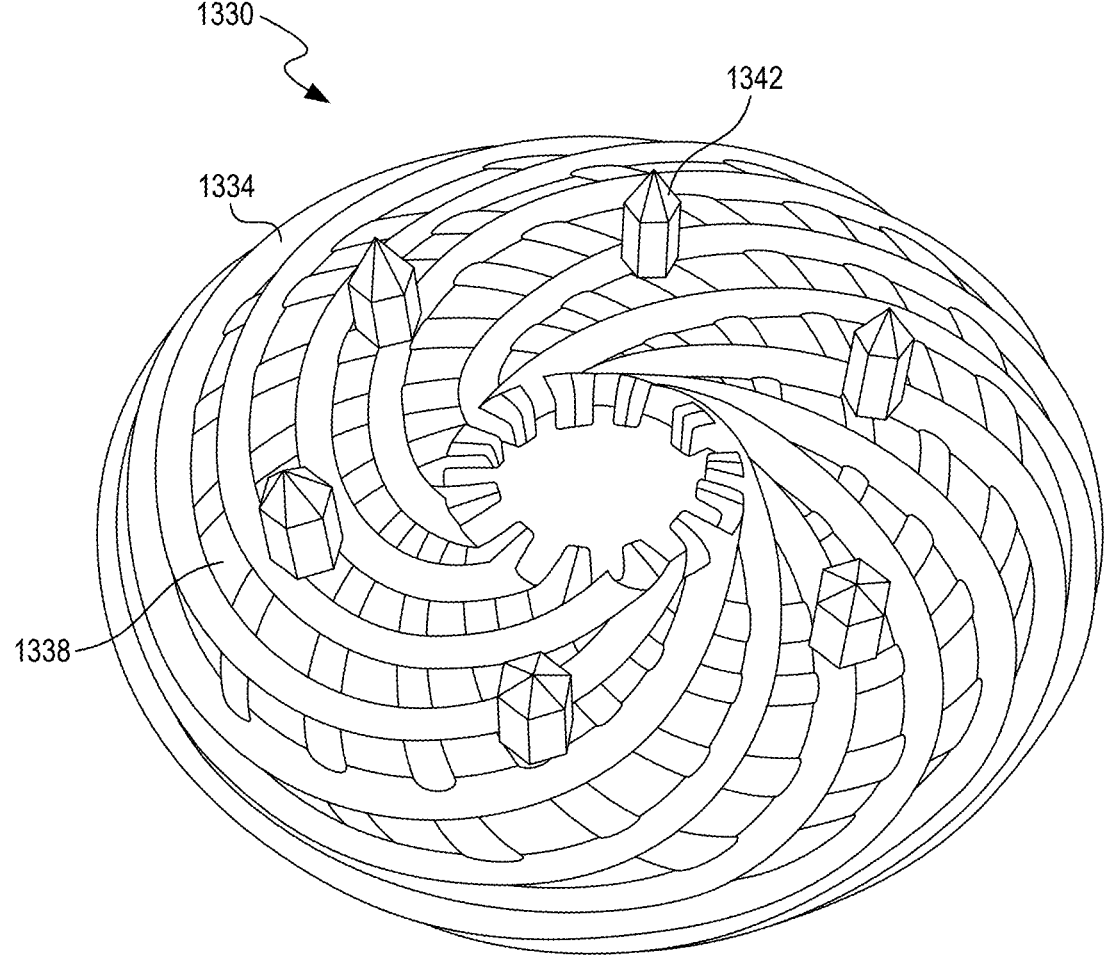
FIG. 13B is a drawing illustrating an example mount for a compact portable electromagnetic field and ion emitter apparatus, in accordance with one or more embodiments.
Figure 13C:
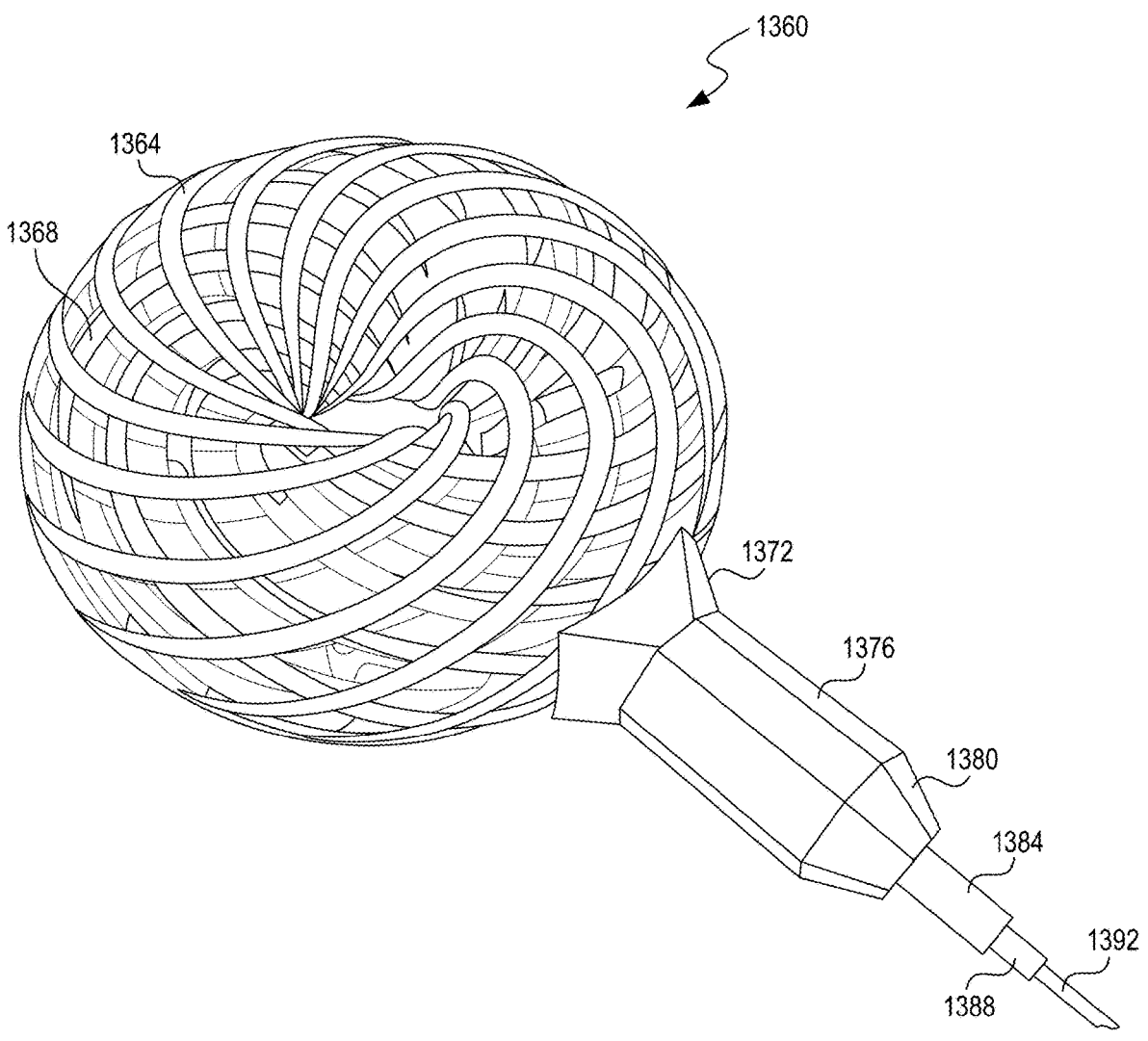
FIG. 13C is a drawing illustrating an example compact portable electromagnetic field and ion emitter apparatus, in accordance with one or more embodiments.

FIG. 13B is a drawing illustrating an example mount 1330 for a compact portable electromagnetic field and ion emitter apparatus, in accordance with one or more embodiments. An example apparatus 1360 is illustrated and described in more detail with reference to FIG. 13C. The apparatus is used for generating electromagnetic fields. In embodiments, the mount 1330 has a first set 1334 of grooves and a second set 1338 of grooves. The grooves of the second set 1338 crisscross the grooves of the first set 1334. Gemstones 1342 are shaped and sized to be embedded in one or more cavities of the mount 1330. Example cavities 1104, 1108 are illustrated and described in more detail with reference to FIG. 11.

FIG. 13C is a drawing illustrating an example compact portable electromagnetic field and ion emitter apparatus 1360, in accordance with one or more embodiments.

The apparatus 1360 includes a coil made of a conducting wire wound around a mount in one of a clockwise configuration or a counterclockwise configuration, such that the coil forms a toroid and has an inductance. An example coil 502 is illustrated and described in more detail with reference to FIG. 5. The coil can be a Qi Coil, POE coil, toroidal nested coil, etc. An example mount 1300 is illustrated and described in more detail with reference to FIG. 13A. The coil is a passive two-terminal electrical component that stores energy in a magnetic field when electrical signals (e.g., electric current) flows through it. In embodiments, the apparatus 1360 includes an insulated wire wound into a coil.

In embodiments, the mount has a first set of grooves and a second set of grooves crisscrossing the first set of grooves. An example first set 1304 of grooves and second set 1308 of grooves is illustrated and described in more detail with reference to FIG. 13A. The coil includes first windings 1368 of the wire wound into the first set of grooves of the mount and second windings of the wire wound into the second set of grooves of the mount. The second windings 1364 overlay the first windings 1368. A winding herein refers to one or more turns of a conducting wire that forms a continuous coil through which an electric current can pass.

When the electrical signals flowing through the coil change, the time-varying magnetic fields induce an electro-motive force (voltage) in the conductor wire. The induced voltage has a polarity (direction) which opposes the change in the currents that created the induced voltage. As a result, the coil opposes changes in current through it. The coil is characterized by its inductance, which is the ratio of the voltage to the rate of change of the current. The mount can have a magnetic core made of iron or ferrite (inside the coil), which serves to increase the magnetic fields and thus the inductance. In embodiments, the wire is twisted to increase a resistance of the wire and a density of the electromagnetic fields. The wire can be shielded to reduce electromagnetic interference.

The wire is made of a conductive metal, such as copper, and the mount can be made of plastic, wood, or a metal, such as iron. The coil is electrically coupled to a user device. An example user device 206 is illustrated and described in more detail with reference to FIG. 2. The coil functions as an inductor to generate electromagnetic fields from electrical signals provided by the user device for providing therapy to a user. In embodiments, the apparatus 1360 incorporates the coil connected to an external amplifier (e.g., within the user device 102 or a wireless amplifier), such that amplified electrical signals from digital audio frequency files are provided to the apparatus 1360 by the user device. An example amplifier 672 is illustrated and described in more detail with reference to FIG. 6C.

In embodiments, the apparatus 1360 includes a cable 1392 that receives electrical signals from an electrical jack plugged into a user device or from a wireless receiver. An example electrical jack 202 is illustrated and described in more detail with reference to FIG. 2. The apparatus 1360 can also include a wireless receiver 1388. The wireless receiver 1388 is an electronic device that receives wireless signals and converts the information carried by them to a usable form. Example wireless signals 720, 724 are illustrated and described in more detail with reference to FIG. 7. The wireless receiver 1388 can include an antenna. The antenna intercepts wireless signals (electromagnetic waves) and con-verts them to tiny alternating currents applied to the receiver 1388, and the receiver 1388 extracts the desired information. In embodiments, the receiver 1388 uses electronic filters to separate the desired electrical signals from other signals picked up by the antenna. In embodiments, the apparatus 1360 includes an amplifier 1384 to amplify the electrical signals.

The apparatus 1360 generates the electromagnetic fields based on the inductance when the electrical signals pass through the coil. In embodiments, the electromagnetic fields include pulsed vortex fields having ELF/VLF frequencies. The pulsed vortex fields can send magnetic energy into a user's body and work with the body's natural magnetic field to improve healing. The pulsed vortex fields can help a user to increase electrolytes and ions, influencing electrical changes on a cellular level and influencing cellular metabo-lism. For example, the pulsed vortex fields can help relieve chronic pain. The generated electromagnetic fields from the apparatus 1360 are configured by the coil to provide therapy to the user.

In embodiments, the electromagnetic fields include a left-hand spin torsion field when the wire is wound in the counterclockwise configuration. The electromagnetic fields include a right-hand spin torsion field when the wire is wound in the clockwise configuration. The clip 1376 is affixed to the mount at a first end 1372 of the clip 1376. The clip 1376 encases terminal ends of the wire. In embodi-ments, the clip 1376 includes a 3.5 mm audio jack disposed at a second end 1380 of the clip 1376. In embodiments, the second end 1380 encloses a portion of the cable 1392, the amplifier 1384, or the wireless receiver 1388. Terminal ends of the wire can be electrically connected to a 3.5 mm audio jack. In embodiments, the clip 1376 is configured to pass the electrical signals from the user device to the coil via a 3.5 mm audio jack.

FIG. 14 is a flow diagram illustrating an example process for using a compact portable electromagnetic field and ion emitter apparatus, in accordance with one or more embodi-ments. In embodiments, the process of FIG. 14 is performed by the example computer system 1500 illustrated and described in more detail with reference to FIG. 15. Particular entities, for example, a base station, a user device, or a system, perform some or all of the steps of the process in other embodiments. An example base station 664 and example system 660 are illustrated and described in more detail with reference to FIG. 6. An example user device 206 is illustrated and described in more detail with reference to FIG. 2. Likewise, embodiments can include different and/or additional steps, or perform the steps in different orders.

In step 1404, digital audio files stored on a user device or base station are selected and played. In embodiments, the user device or apparatus receives digital audio files from a server or the cloud. Example digital audio files 802 are illustrated and described in more detail with reference to FIG. 8. The digital audio files include frequencies in an ELF range and a VLF range. The ELF range includes electromagnetic radiation (radio waves) having frequencies from 3 hertz (Hz) to 30 Hz, and corresponding wavelengths of 100,000 to 10,000 kilometers (km), respectively. The VLF range includes radio frequencies (RF) in the range of 3-30 kilohertz (kHz), corresponding to wavelengths from 100 to 10 km, respectively. The audio files are converted to electrical signals by the user device or base station.

In step 1408, the user device or base station amplifies the electrical signals. The electrical signals have the frequencies of the audio files. In embodiments, the user device includes a built-in amplifier that increases the power of the audio (electrical) signals (time-varying voltage or current). An example amplifier 672 is illustrated and described in more detail with reference to FIG. 6C. The amplifier uses electric power from a power supply to increase the amplitude of the electrical signals, producing proportionally greater amplitude signals at its output. The amount of amplification provided by the amplifier is measured by its gain: the ratio of output voltage, current, or power to input. In embodiments, the amplifier is located within a base station or another device, e.g., the apparatus 704 illustrated and described in more detail with reference to FIG. 7.

In step 1412, the electrical signals are sent to an apparatus for generating therapeutic electromagnetic fields. An example apparatus 1360 is illustrated and described in more detail with reference to FIG. 13C. The apparatus is configured to generate electromagnetic fields. In embodiments, the user device or base station has a wireless transmitter implemented using components of the example computer system 1500 illustrated and described in more detail with reference to FIG. 15. An example transmitter 692 is illustrated and described in more detail with reference to FIG. 6C. The transmitter transmits the electrical signals to the apparatus wirelessly. The apparatus has a wireless receiver implemented using components of the example computer system 1500 illustrated and described in more detail with reference to FIG. 15. An example wireless receiver 1388 is illustrated and described in more detail with reference to FIG. 13C. The apparatus can also have an amplifier built in for amplifying the received electrical signals. An example amplifier 1384 is illustrated and described in more detail with reference to FIG. 13C.

In embodiments, the apparatus includes an electrical jack that is plugged into an electrical socket of the user device. The electrical jack can be a Lightning audio jack, a micro jack 2.5, a 3.5 mm mini-jack, a 6.3 mm jack, a USB audio jack, a Type-C jack, etc. An example electrical jack 202 and example electrical socket 204 are illustrated and described in more detail with reference to FIG. 2. For example, a clip of the apparatus can include a 3.5 mm audio jack. An example clip 1376 is illustrated and described in more detail with reference to FIG. 13C. Wires of the apparatus are electrically connected to the 3.5 mm audio jack. The apparatus is configured to pass the electrical signals from the user device to a coil of the apparatus via the 3.5 mm audio jack.

In step 1416, the electromagnetic fields are generated using a coil based on an inductance of the coil by passing the electrical signals from the electrical jack through the coil. An example coil 502 is illustrated and described in more detail with reference to FIG. 5. The electromagnetic fields are configured by the coil to provide therapy to a user proximate to the apparatus. In embodiments, the electromagnetic fields include pulsed vortex fields having the frequencies of the audio files. Ions can be generated in the presence of the electromagnetic fields using one or more gemstones of the system. An example gemstone 1320 is illustrated and described in more detail with reference to FIG. 13A. The ions are for providing the therapy to the user. In embodiments, the coil includes a wire wound in one of a clockwise configuration or a counterclockwise configuration. An example wire (windings 1364) is illustrated and described in more detail with reference to FIG. 13C. The electromagnetic fields include a left-hand spin torsion field when the wire is wound in the counterclockwise configuration. The electromagnetic fields include a right-hand spin torsion field when the wire is wound in the clockwise configuration.

Figure 15:
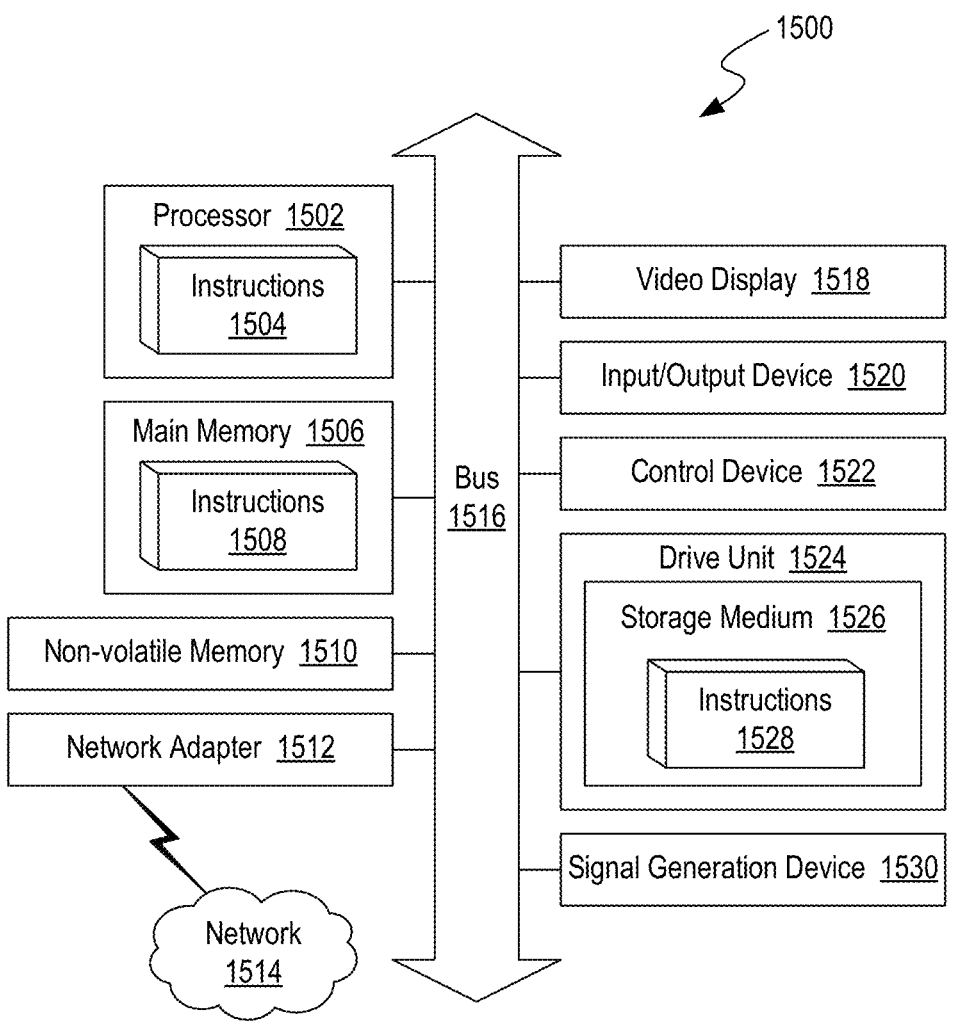
FIG. 15 is a block diagram illustrating an example computer system, in accordance with one or more embodiments.

FIG. 15 is a block diagram illustrating an example computer system 1500, in accordance with one or more embodiments. Components of the example computer system 300 can be used to implement, e.g., the user device 102, the clip 108, and the portable electromagnetic field and ion emitter apparatus 704 illustrated and described in more detail with reference to FIGS. 1 and 7. At least some operations described herein can be implemented on the computer system 1500.

The computer system 1500 can include one or more central processing units ("processors") 1502, main memory 1506, non-volatile memory 1510, network adapters 1512 (e.g., network interface), video displays 1518, input/output devices 1520, control devices 1522 (e.g., keyboard and pointing devices), drive units 1524 including a storage medium 1526, and a signal generation device 1530 that are communicatively connected to a bus 1516. The bus 1516 is illustrated as an abstraction that represents one or more physical buses and/or point-to-point connections that are connected by appropriate bridges, adapters, or controllers. The bus 1516, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), an IIC (I2C) bus, or an Institute of Electrical and Electronics Engineers (IEEE) standard 1394 bus (also referred to as "Firewire").

The computer system 1500 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 1500.

While the main memory 1506, non-volatile memory 1510, and storage medium 1526 (also called a "machine-readable medium") are shown to be a single medium, the terms "machine-readable medium" and "storage medium" should be taken to include a single medium or multiple media (e.g., a centralized/distributed database and/or associated caches and servers) that store one or more sets of instructions 1528. The terms "machine-readable medium" and "storage medium" shall also be taken to include any medium that is capable of storing, encoding, or carrying a set of instructions for execution by the computer system 1500.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 1504, 1508, 1528) set at various times in various memory and storage devices in a computer device. When read and executed by the one or more processors 1502, the instruction(s) cause the computer system 1500 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine- or computer-readable media used to actually effect the distribution.

Further examples of machine-readable storage media, machine-readable media, or computer-readable media include recordable-type media such as volatile and non-volatile memory devices 1510, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 1512 enables the computer system 1500 to mediate data in a network 1514 with an entity that is external to the computer system 1500 through any communication protocol supported by the computer system 1500 and the external entity. The network adapter 1512 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 1512 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 16:
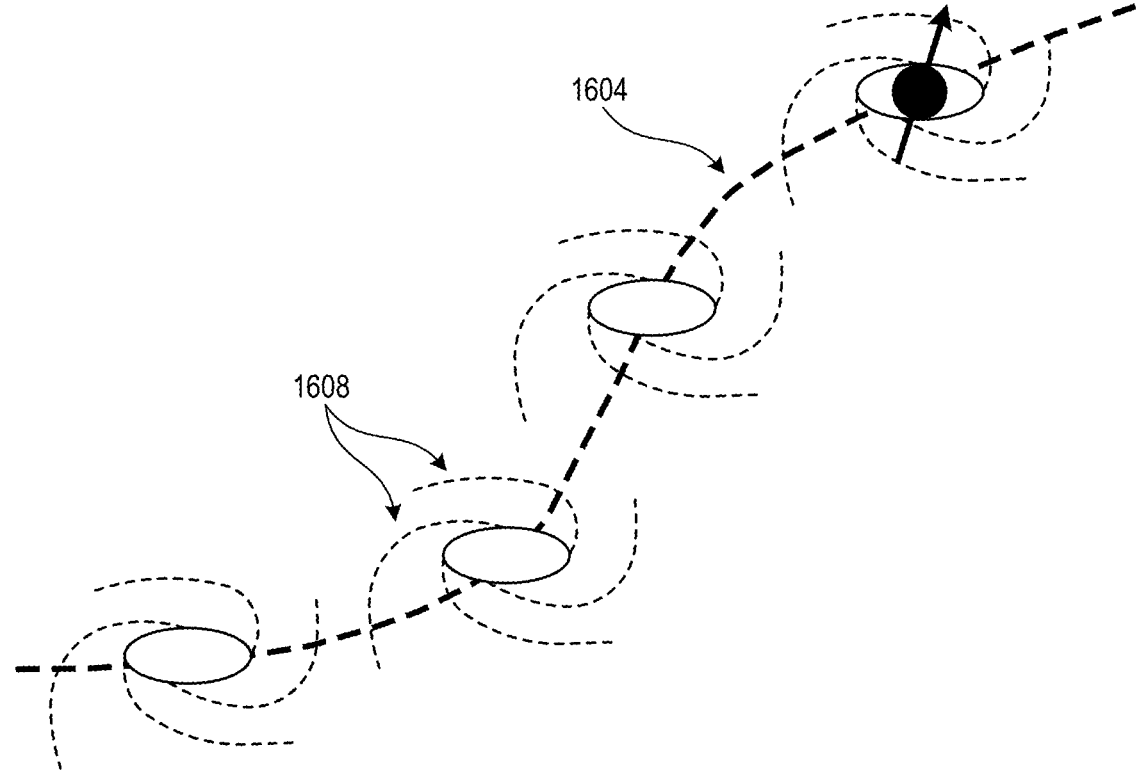
FIG. 16 is a drawing illustrating example electromagnetic fields including spin torsion fields, in accordance with one or more embodiments.

FIG. 16 is a drawing illustrating example electromagnetic fields including spin torsion fields, in accordance with one or more embodiments. When a particle accelerates rapidly on a path 1604, it leaves behind in its wake ripples from its rotating energy pattern. When the particle moves at a constant speed, the incoming and outgoing ripples are in balance, but when accelerating, the particle is no longer where the returning waves "thought" it would be. As a result, the particle leaves behind ripples 1608 resembling tiny vortexes of flow in the vacuum. When a spinning particle accelerates or its spin direction changes, its radiation field of outgoing and incoming energy also changes. This gives rise to additional "twisting" or torsion in the space itself.

In embodiments, the electromagnetic fields generated by the apparatuses described herein include a left-hand spin torsion field when wire of the apparatus is wound in a counterclockwise configuration. An example apparatus 1360 and wire (windings 1364) are illustrated and described in more detail with reference to FIG. 13C. The electromagnetic fields include a right-hand spin torsion field when the wire is wound in a clockwise configuration.

Figure 17A:
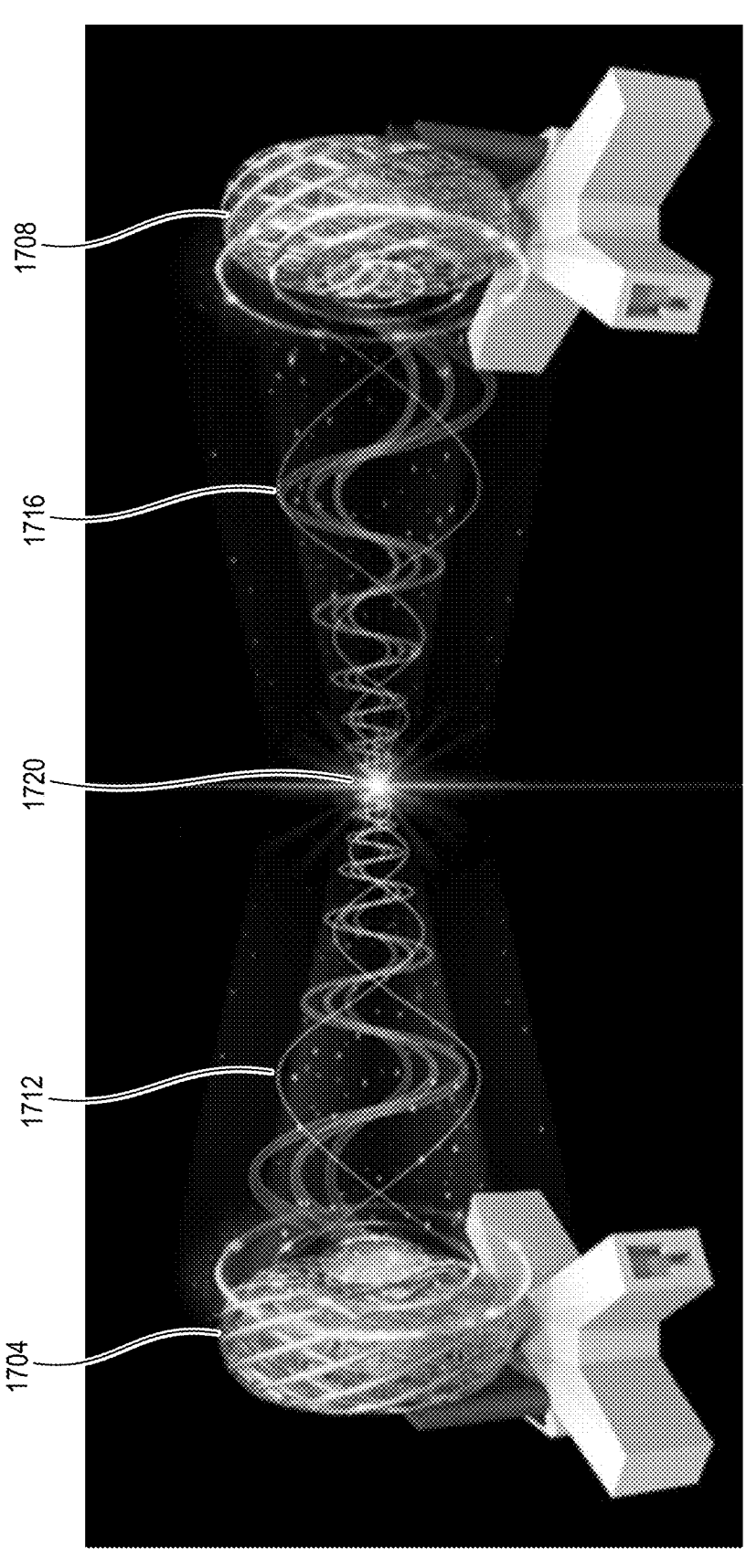
FIG. 17A is a drawing illustrating an example pair of electromagnetic field generating apparatuses, in accordance with one or more embodiments.

FIG. 17A is a drawing illustrating an example pair of electromagnetic field generating apparatuses 1704, 1708, in accordance with one or more embodiments. In embodiments, the electromagnetic fields 1712, 1716 generated by the pair 1704, 1708 include pulsed vortex fields having ELF/VLF frequencies. In embodiments, the electromagnetic fields include a torsion field 1712 having a directional spin. Using a coil in proximity to one or more other coils producing other electromagnetic fields 1716 having opposing spins generates a phase-conjugated torsion field 1720. Phase conjugation is a physical transformation of a wave field where the resulting field has a reversed propagation direction but keeps its amplitudes and phases. Acoustic phase conjugation occurs when sound velocity is modulated by an electromagnetic field. For example, the generation of a conjugate wave represents the decay of a photon into two phonons. The two phonons have opposite wave vectors k and –k (i.e., they will propagate in opposite directions) and a frequency two times smaller than that of the photon.

Figure 17B:
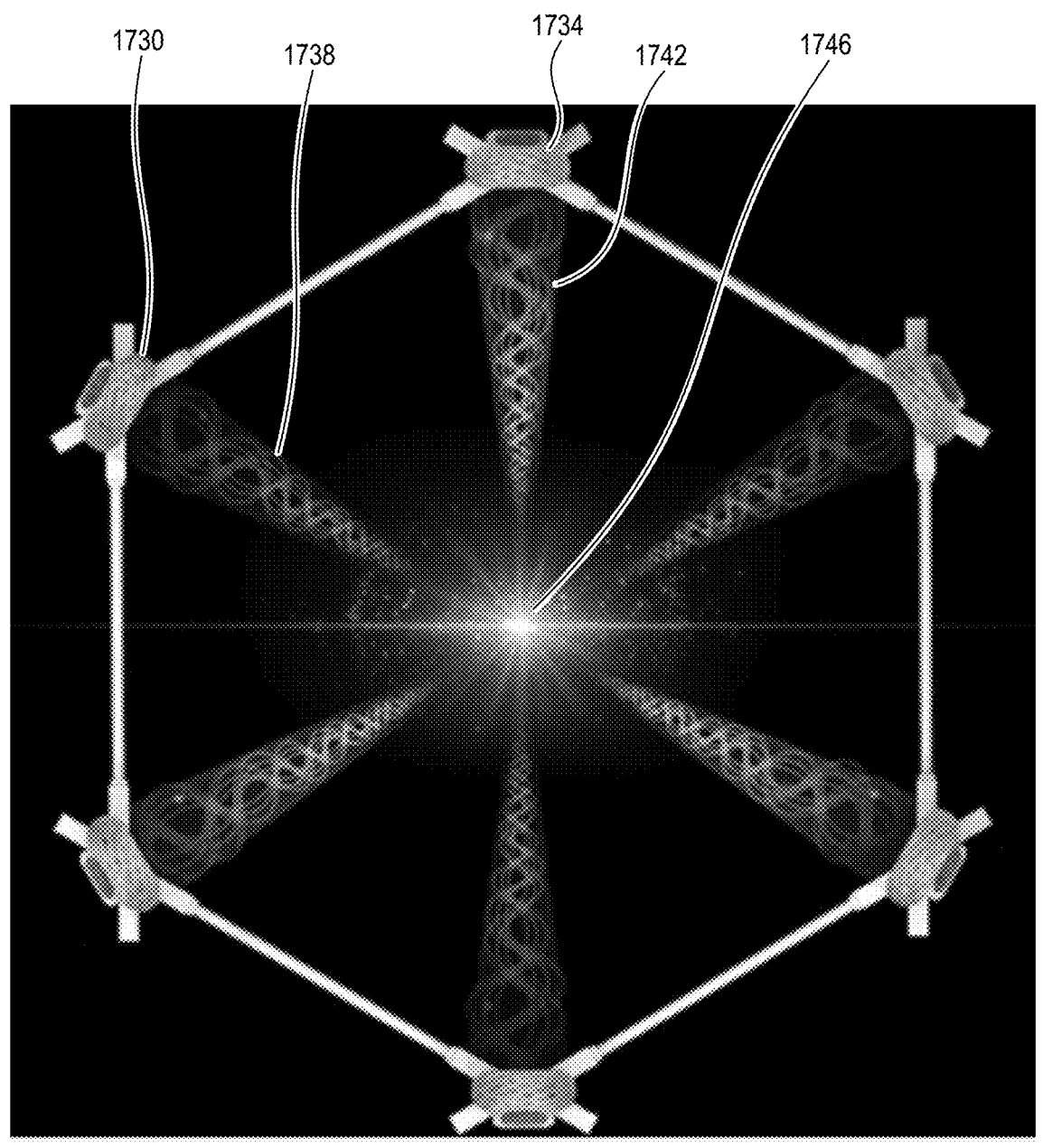
FIG. 17B is a drawing illustrating an example group of six electromagnetic field generating apparatuses, in accordance with one or more embodiments.

FIG. 17B is a drawing illustrating an example group of six electromagnetic field generating apparatuses 1730, 1734, etc., in accordance with one or more embodiments. In embodiments, the electromagnetic fields 1738, 1742, etc., generated by the apparatuses 1730, 1734, etc., include pulsed vortex fields having ELF/VLF frequencies. In embodiments, the electromagnetic fields include a torsion field 1738 having a directional spin. Using a coil in proximity to one or more other coils producing other electromagnetic fields 1742 having opposing spins generates a phase-conjugated torsion field 1746.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

I claim:

1. An apparatus comprising:

a torus-shaped mount; and a coil comprising a conducting wire wound around the mount such that the coil has an inductance, the coil configured to:

generate electromagnetic fields based on the inductance when electrical signals pass through the coil, the electromagnetic fields having frequencies in an Extremely Low Frequency (ELF) range and a Very Low Frequency (VLF) range, the electromagnetic fields to provide therapy to a user; and a clip affixed to the mount and encasing terminal ends of the wire, the clip configured to:

receive the electrical signals from a user device via an electrical jack electrically coupled to the terminal ends; and pass the electrical signals to the coil via the terminal ends, wherein the mount has a first set of grooves and a second set of grooves crisscrossing the first set of grooves, and wherein the coil comprises:

first windings of the wire wound into the first set of grooves of the mount, and second windings of the wire wound into the second set of grooves of the mount, the second windings overlaying the first windings.

2. The apparatus of claim 1, wherein the coil forms a toroid, and wherein the wire is wound around the mount in one of:

a clockwise configuration; or a counterclockwise configuration.

3. The apparatus of claim 1, wherein the electrical signals are generated by the user device from amplification of digital audio files stored on the user device.

4. The apparatus of claim 1, wherein the mount has one or more longitudinal cavities, the apparatus comprising:

one or more gemstones shaped and sized to be embedded in the one or more cavities.

5. The apparatus of claim 1, wherein the wire is twisted to increase a resistance of the wire and a density of the electromagnetic fields, and wherein the wire is shielded to reduce electromagnetic interference.

6. The apparatus of claim 1, wherein the clip is shaped and sized to be grasped by a hand of the user, the clip is affixed to the mount at an end of the clip, and the terminal ends of the wire enter the clip from the coil at the end of the clip.

7. The apparatus of claim 1, wherein the clip comprises the electrical jack, and wherein the electrical jack is disposed at an end of the clip.

8. The apparatus of claim 1, wherein the electrical jack is configured to be inserted into an electrical socket of the user device for passing the electrical signals from the user device to the apparatus.

9. The apparatus of claim 1, wherein the clip comprises a wireless receiver configured to:

receive wireless signals generated by a wireless transmitter of the user device, the wireless signals corresponding to amplified digital audio files stored on the user device; and generate the electrical signals from the wireless signals.

10. The apparatus of claim 1, wherein the mount comprises plastic or wood.

11. The apparatus of claim 1, wherein the wire comprises copper.

12. The apparatus of claim 1, wherein the electrical jack comprises a 3.5 mm audio jack.

13. The apparatus of claim 1, wherein each groove of the first set of grooves lies between two ridges of the mount.

14. The apparatus of claim 1, wherein each groove of the second set of grooves lies between two ridges of the mount.

15. The apparatus of claim 1, wherein the clip is configured to support the mount.

16. The apparatus of claim 1, wherein the electromagnetic fields have frequencies between 3 Hz and 30 KHz.

17. The apparatus of claim 1, wherein the apparatus is portable.

* * * * *